(12) United States Patent
Stewart et al.

(10) Patent No.: US 6,355,412 B1
(45) Date of Patent: Mar. 12, 2002

(54) METHODS AND COMPOSITIONS FOR DIRECTED CLONING AND SUBCLONING USING HOMOLOGOUS RECOMBINATION

(75) Inventors: A. Francis Stewart, Leimen; Youming Zhang, Heidelberg, both of (DE); Joep Pieter Paul Muyrers, Meerssen (NL)

(73) Assignee: The European Molecular Biology Laboratory, Heidelberg (DE)

( * ) Notice: Subject to any disclaimer, the term of this patent is extended or adjusted under 35 U.S.C. 154(b) by 0 days.

(21) Appl. No.: 09/350,830

(22) Filed: Jul. 9, 1999

(51) Int. Cl.$^7$ .......................... C12Q 1/00; C12Q 1/68; C12N 15/64; C12N 15/63; C12N 1/21; C12N 5/10; C12N 1/20; C07H 21/04
(52) U.S. Cl. .............................. 435/4; 435/6; 435/91.4; 435/320.1; 435/252.8; 435/252.1; 435/325; 536/23.1
(58) Field of Search ................... 435/91.41, 252.33, 435/320.1, 91.4, 252.83, 325, 4, 6, 252.1; 536/23.1, 24.1

(56) References Cited

U.S. PATENT DOCUMENTS 5,792,633 A * 8/1998 Schiestl et al. .......... 435/172.3

FOREIGN PATENT DOCUMENTS

| WO | WO 98/59060 | 12/1998 |
|---|---|---|
| WO | WO 99/29837 | 6/1999 |

OTHER PUBLICATIONS

Zhang et al., "DNA cloning by homologous recombination in *Escherichia coli*", Nat Biotechnol 2000 Dec; 18(12):1314–7.
Ausubel et al. (eds.), 1988, *Current Protocols in Molecular Biology*, vol. 1, Green Publishing Associates and John Wiley & Sons, NY, pp. 2.10–2.10.16.
Bhargava J, et al., "pPAC–ResQ: A yeast–bacterial shuttle vector for capturing inserts from P1 and PAC clones by recombinogenic targeted cloning", Genomics. Mar. 15, 1999;56(3):337–9.
Bubeck P et al., "Rapid cloning by homologous recombination in vivo", Nucleic Acids Res. JUl. 25, 1993;21(15):3601–2.
Chartier C et al., "Efficient generation of recombinant adenovirus vectors by homologous recombination in *Escherichia coli*", J Virol. Jul. 1996;70(7):4805–10.
Degryse E., "In vivo intermolecular recombination in *Escherichia coli*: application to plasmid constructions", Gene. Apr. 17, 1996;170(1):45–50.
Gillen JR et al., "Characterization of the deoxyribonuclease determined by lambda reverse as exonuclease VIII of *Escherichia coli*", J Mol Biol. Jun. 15, 1977;113(1):27–41.
Gillen JR et al., "Genetic analysis of the RecE pathway of genetic recombination in *Escherichia coli* K–12", J Bacteriol. Jan. 1981;145(1):521–32.

Grunstein M et al., "Colony hybridization: a method for the isolation of cloned DNAs that contain a specific gene", Proc Natl Acad Sci U S A. Oct. 1975;72(10):3961–5.
Hall and Kolodner, 1994, "Homologous pairing and strand exchange promoted by the *Escherichia coli* RecT protein", Proc Natl Acad Sci U S A. Apr. 12, 1994;91(8):3209–9.
Hall SD et al., "Identification and characterization of the *Escherichia coli* RecT protein, a protein encoded by the recE region that promotes renaturation of homologous single–stranded DNA", J Bacteriol. Jan. 1993;175(1):277–87.
HalletB et al., "Transposition and site–specific recombination: adapting DNA cut–and–paste mechanisms to a variety of genetic rearrangements", FEMS Microbiol Rev. Sep. 1997;21(2):157–78.
He TC et al., "A simplified system for generating recombinant adenoviruses", Proc Natl Acad Sci U S A. Mar. 3, 1998;95(5):2509–14.
Helinski et al., 1996, *Escherichia coli and Salmonella: Cellular and Molecular Biology*, $2^{nd}$ edition, Niedhardt (ed.), ASM Press, Washington, ISBN 1–55581–084–5.
Jermutus L et al., "Recent advances in producing and selecting functional proteins by using cell–free translation", Curr Opin Biotechnol. Oct. 1998;9(5):534–48.
Joseph and Kolodner, "Exonuclease VIII of *Escherichia coli*. I. Purification and physical properties", J Biol Chem. Sep. 10, 1993;258(17):10411–7.
Keim and Lark, "The RecE recombination pathway mediates recombination between partially homologous DNA sequences: structural analysis of recombination products", J Struct Biol. 1990 Jul.–Sep.;104(1–3):97–106.
Kmiec and Hollomon, "Beta protein of bacteriophage lambda promotes renaturation of DNA", J Biol Chem. Dec. 25, 1981;256(24):12636–9.
Kolodner R, "Homologous pairing proteins encoded by the *Escherichia coli* recE and recT genes", Mol Microbiol. Jan. 1994;11(1):23–30.
Little JW., "An exonuclease induced by bacteriophage lambda. II. Nature of the enzymatic reaction", J Biol Chem. Feb. 25, 1967;242(4):679–86.
Luisi–DeLuca C, "Genetic and physical analysis of plasmid recombination in recB recC sbcB and recB recC sbcA *Escherichia coli* K–12 mutants", Genetics. Jun. 1989;122(2):269–78.

(List continued on next page.)

Primary Examiner—Robert A. Schwartzman
Assistant Examiner—Katharine F Davis
(74) Attorney, Agent, or Firm—Pennie & Edmonds LLP

(57) ABSTRACT

The present invention is directed to methods and compositions for DNA subcloning using bacterial recombinase–mediated homologous recombination. The invention relates to methods for cloning, compositions comprising polynucleotides usefall as cloning vectors, cells comprising such polynucleotide compositions, and kits useful for cloning mediated by bacterial recombinases, such as RecE/T and Redα/β.

54 Claims, 8 Drawing Sheets

OTHER PUBLICATIONS

Figure 1A:
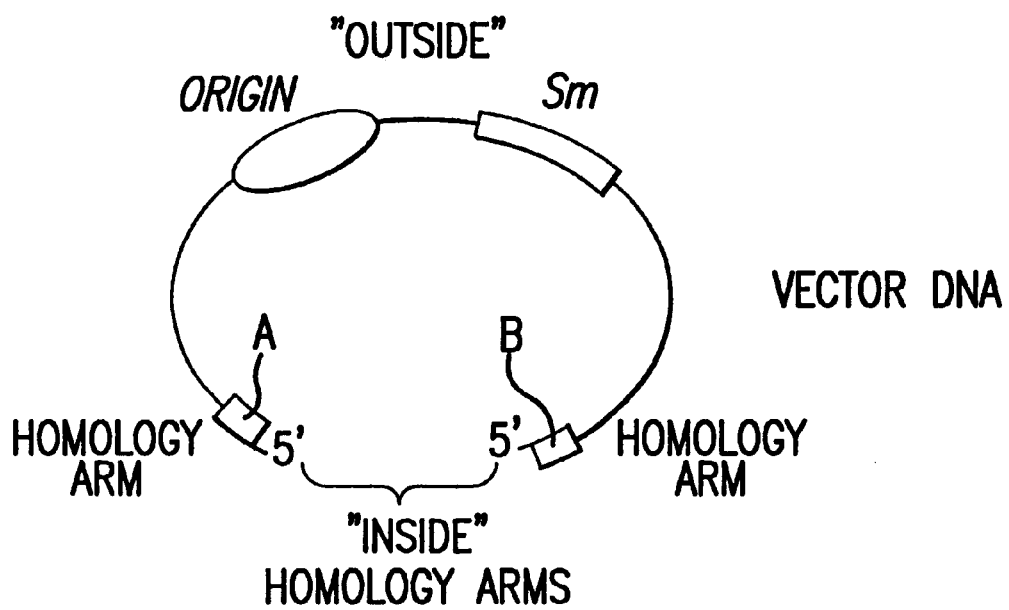

Messerle M et al., "Cloning and mutagenesis of a herpesvirus genome as an infectious bacterial artificial chromosome", Proc Natl Acad Sci U S A. Dec. 23, 1997;94(26):14759–63.

Miller, 1992, *A Short Course in Bacterial Genetics*, Cold Spring Harbor Laboratory Press, NY, pp. 10.4–10.11.

Mullins LJ et al., "Efficient Cre–Iox linearisation of BACs: applications to physical mapping and generation of transgenic animals", Nucleic Acids Res. Jun. 15, 1997;25(12):2539–40.

Muniyappa and Radding, "The homologous recombination system of phage lambda. Pairing activities of beta protein", J Biol Chem. Jun. 5, 1986;261(16):7472–8.

Murphy KC, "Lambda Gam protein inhibits the helicase and chi–stimulated recombination activities of *Escherichia coli* RecBCD enzyme", J Bacteriol. Sep. 1991;173(18):5808–21.

Muyrers JP et al., "Rapid modification of bacterial artificial chromosomes by ET–recombination", Nucleic Acids Res. Mar. 15, 1999;27(6):1555–7.

Nunes–Duby SE et al., "Similarities and differences among 105 members of the Int family of site–specific recombinases", Nucleic Acids Res. Jan. 15, 1998;26(2):391–406.

Nussbaum A, "Restriction–stimulated homologous recombination of plasmids by the RecE pathway of *Escherichia coli*", Genetics. Jan. 1992;130(1):37–49.

Oliner JD et al., "In vivo cloning of PCR products in *E. coli*", Nucleic Acids Res. Nov. 11, 1993:21(22):5192–7.

Passy SI et al., "Rings and filaments of beta protein from bacteriophage lambda suggest a superfamily of recombination proteins", Proc Natl Acad Sci U S A. Apr. 13, 1999;96(8):4279–84.

Poteete AR and Fenton AC, "DNA–binding properties of the Erf protein of bacteriophage P22", J Mol Biol. Jan. 15, 1983;163(2):257–75.

Radding and Carter, "The role of exonuclease and beta protein or phage lambda in genetic recombination. 3. Binding to deoxyribonucleic acid", J Biol Chem. Apr. 25, 1971;246(8):2513–8.

Raymond CK et al., "General method for plasmid construction using homologous recombination", Biotechniques. Jan. 1999; 26(1):134–8, 140–1.

Reyrat JM et al., "Counterselectable markers: untapped tools for bacterial genetics and pathogenesis", Infect Immun. Sep. 1998;66(9):4011–7.

Ringrose L et al., "The Kw recombinase, an integrase from *Kluyveromyces waltii*", Eur J Biochem. Sep. 15, 1997;248(3):903–12.

Sauer B., "Site–specific recombination: developments and applications", Curr Opin Biotechnol. Oct. 1994;5(5):521–7.

Stark WM et al., "Catalysis by site–specific recombinases", Trends Genet. Dec. 1992;8(12):432–9.

Szostak JW et al., "The double–strand–break repair model for recombination", Cell. May 1983;33(1):25–35.

Utatsu I et al., "Yeast plasmids resembling 2 micron DNA: regional similarities and diversities at the molecular level", J Bacteriol. Dec. 1987;169(12):5537–45.

Yang XW et al., "Homologous recombination based modification in *Escherichia coli* and germline transmission in transgenic mice of a bacterial artifical chromosome", Nat Biotechnol. Sep. 1997;15(9):859–65.

Zhang Y et al., "A new logic for DNA engineering using recombination in *Escherichia coli*", Nat Genet. Oct. 1998;20(2):123–8.

www.ncbi.nlm.nih.gov (National Center for Biotechnology Information) Genbank Accession No. J02459. Bacteriophage lambda, complete genome. Apr. 10, 1996. Accessed on: Jan. 4, 2000.

www.ncbi.nlm.nih.gov (National Center for Biotechnology Information) Genbank Accession No. M24905. *Escherichia coli* racC and recE genes, complete cds and 5' end. Database [Online]. Last update: Nov. 10, 1993. Accessed on: Jan. 4, 2000.

www.ncbi.nlm.nih.gov (National Center for Biotechnology Information) Genbank Accession No. L23927. *Escherichia coli* exonuclease VIII (recE) gene, 3' end, and recT gene, complete cds. Database [Online]. Last update: Jan. 31, 1994. Accessed on: Jan. 4, 2000.

www.ncbi.nlm.nih.gov (National Center for Biotechnology Information) Genbank Accession No. M17233. Bacteriophage lambda, complete genome. Database [Online]. Last update: Apr. 10, 1996. Accessed on: Jan. 4, 2000.

www.expasy.ch/sprot/ (SWISS–PROT Annotated protein sequence database TrEMBL Computer–annotated supplement to Swiss–Prot) SWISS–PROT Accession No. P15033. RACC_ECOLI. Database [Online]. Last update: Apr. 14, 1990. Accessed on: Jan. 4, 2000.

www.expasy.ch/sprot/ (SWISS–PROT Annotated protein sequence database TrEMBL Computer–annotated supplement to SWISS–PROT) SWISS–PROT Accession No. P33228. RECT_ECOLI. Database [Online]. Last update: Feb. 28, 1994. Accessed on: Jan. 4, 2000.

\* cited by examiner

METHODS AND COMPOSITIONS FOR DIRECTED CLONING AND SUBCLONING USING HOMOLOGOUS RECOMBINATION

TABLE of CONTENTS

1. INTRODUCTION
2. BACKGROUND OF THE INVENTION
3. SUMMARY OF THE INVENTION
4. DESCRIPTION OF THE FIGS.
5. DETAILED DESCRIPTION OF THE INVENTION
   5.1 Methods for Cloning and Subcloning by Homologous Recombination
      5.1.1 Approach 1: Introduction of Vector into Host Cell Containing Target DNA
      5.1.2 Approach 2: Co-Introduction of Vector and Target DNA into the Host Cell
      5.1.3 Approach 3: Introduction of Target DNA into Host Cells Containing Vector DNA
   5.2 Compositions for Cloning and Subcloning by Homologous Recombination
      5.2.1 The Homology Cloning Vector
         5.2.1.1 The Origin of Replication
         5.2.1.2 The Selectable Marker
         5.2.1.3 the Homology Arms
         5.2.1.4 Adapter Oligonucleotide Homology Arms
         5.2.1.5 Construction of the Vector
      5.2.2 Bacterial Recombinases
         5.2.2.1 Protein Expression
      5.2.3 Host Cells
      5.2.4 Target DNA
   5.3 Methods for use of the Invention
      5.3.1 Introduction of DNA into Host Cells
      5.3.2 Oligonucleotides
      5.3.3 DNA Amplification
   5.4 Methods for Diagnostic Applications
      5.4.1 Detection of Foreign DNA
      5.4.2 Diagnosis of Mutations and Polymorphisms in Cellular DNA
   5.5 Kits
6. EXAMPLE: RECE/T AND RED$\alpha$/$\beta$ SUBCLONING
   6.1 Methods and Materials
   6.2 Results

1. INTRODUCTION

The present invention is directed to methods and compositions for DNA cloning and subcloning using bacterial recombinase-mediated homologous recombination. In a specific embodiment, RecE/T or Red$\alpha$/$\beta$ recombinases, or any functionally equivalent system for initiating bacterial homologous recombination, such as erf from phage P22, are used. In particular, the invention relates to cloning methods, diagnostic methods, compositions comprising polynucleotides useful as cloning vectors, cells comprising such polynucleotide compositions, and kits useful for RecE/T and Red$\alpha$/$\beta$ mediated cloning.

2. BACKGROUND OF THE INVENTION

DNA cloning and subcloning in *E. coli* are fundamental to molecular biology. DNA cloning refers to the process whereby an origin of replication is operably linked to a double-stranded DNA fragment, and propagated in *E. coli*, or other suitable host. DNA subcloning refers to the process whereby a double-stranded DNA fragment is taken from a DNA molecule that has already been amplified, either in vitro, for example by PCR, or in vivo by propagation in *E. coli* or other suitable host, and is then linked to an operable origin of replication. Cloning and subcloning in *E. coli* is typically performed by ligating the ends of a DNA fragment to the ends of a linearized vector containing an *E. coli* origin of replication and a selectable marker. The selectable marker is included in the vector to ensure that the newly cloned product, the plasmid containing the insert, is retained and propagated when introduced into its *E. coli* host cell.

Conventional cloning methods have certain limitations. For example, since conventional cloning requires the use of restriction enzymes, the choice of DNA fragments is limited by the availability of restriction enzyme recognition sites in the DNA region of interest. Restriction sites must be found that cut the boundaries of, but not within, the desired DNA fragment. Since most useful restriction enzymes cut fairly frequently, the size of the linear DNA fragment made is also limited.

The increasing use of the polymerase chain reaction (PCR) for generating DNA fragments presents a second major drawback to conventional subcloning. The ends of PCR products are inefficient in ligation reactions due to non-templated nucleotides added to the 3' termini of amplified PCR products by thermostabile polymerase. Furthermore, the use of PCR entails a high risk of mutations. Thus, molecular biologists have searched for new, more effective methods for cloning fragments of DNA, particularly when such fragments are longer than those conveniently accessible by restriction enzyme or PCR methodologies.

Homologous recombination is an alternative approach for cloning and subcloning DNA fragments. Methods for subcloning PCR products in *E. coli* that exploit the host's homologous recombination systems have been described (Oliner et al., 1993, Nucleic Acids Res. 21:5192–97; Bubeck et al., 1993, Nucl. Acids. Res. 21:3601–3602). In such methods, PCR primers, designed to contain terminal sequences homologous to sequences located at the ends of a linearized vector, are used to amplify a DNA fragment of interest. The PCR product and the linearized vector are then introduced into *E. coli*. Homologous recombination within the *E. coli* host cell results in insertion of the PCR product sequences into the plasmid vector. Although these methods have been shown to be useful for subcloning PCR fragments, they have not been applied to subcloning long DNA fragments, or to cloning DNA fragments of any size.

Another method describes an in vivo subcloning method in which two linear DNA molecules, one of which has an origin of replication, and which have long regions of homology at their ends, are used to transform an *E. coli* sbcBC host cell. Homologous recombination occurs in vivo, and results in circularization and propagation of the newly formed plasmid (Degryse, 1996, Gene 170:45). Subsequently, the ability of *E. coli* sbcBC host cells to mediate homologous recombination has been applied to subcloning large DNA fragments from adenovirus and herpes virus genomic DNAs (Chartier et al., 1996, J. Virol. 70: 4805; Messerle, et al., 1997, Proc. Natl. Acad. Sci. USA 94, 14759–14763; He, 1998, Proc. Natl Acad. Sci. USA 95:2509–2514). As described, each subcloning by homologous recombination in *E. coli* sbcBC host cells requires at least two preparatory subcloning steps to position long homology regions either side of an *E. coli* origin of replication. Furthermore, DNA cloning in *E. coli* sbcBC strains has not been described.

Recently, homologous recombination, mediated by either RecE/RecT (RecE/T) or Red$\alpha$/Red$\beta$ (Red$\alpha$/$\beta$) has been shown to be useful for manipulating DNA molecules in *E. coli* (Zhang et al, 1998, Nature Genetics, 20, 123–128; Muyrers et al., 1999, Nucleic Acids Res. 27: 1555–1557). These papers show that, in *E. coli,* any intact, independently replicating, circular DNA molecule can be altered by RecE/T or Redα/β mediated homologous recombination with a linear DNA fragment flanked by short regions of DNA sequence identical to regions present in the circular molecule. Integration of the linear DNA fragment into the circular molecule by homologous recombination replaces sequences between its flanking sequences and the corresponding sequences in the circular DNA molecule.

Citation of a reference herein shall not be construed as an admission that such is prior art to the present invention.

3. SUMMARY OF THE INVENTION

The present invention provides methods and compositions for DNA cloning and subcloning using bacterial recombinase-mediated homologous recombination. The bacterial recombinase is preferably RecE/T and/or Redα/β. Methods can be used to clone, subclone, propagate, and amplify a polynucleotide or mixture of polynucleotides of interest using a vector comprising short regions of DNA homologous to sequences flanking a designated target DNA sequence of interest and an origin of replication.

In one embodiment, the invention provides a method for introducing a double-stranded target DNA into a vector comprising culturing a bacterial cell that expresses a functional recombinase, said bacterial cell containing (a) the target DNA comprising a first double-stranded terminus and a second double-stranded terminus, and (b) a vector DNA comprising, in the following order along the vector DNA strand: (i) a first double-stranded homology arm (ii) an origin of replication; and (iii) a second double-stranded homology arm, such that the sequence of a vector DNA strand of the first homology arm is homologous to the sequence of a target DNA strand of the first terminus, and the sequence of a vector DNA strand of the second homology arm is homologous to the sequence of the target DNA strand of the second terminus, such that the target DNA is inserted into the vector DNA between the homology arms.

In another embodiment, a method is provided for making a recombinant DNA molecule comprising: a) introducing a double-stranded vector into a cell, said cell containing a double-stranded target DNA and expressing a bacterial recombinase, said vector comprising an origin of replication and two homology arms, in the following order from 5' to 3' along a vector DNA strand: a first homology arm, one strand of the origin of replication, and a second homology arm; said target DNA comprising a target DNA sequence and two termini, in the following order, from 3' to 5' along a target DNA strand: a first terminus, the target DNA sequence, and a second terminus, such that the sequence of the first homology arm on said vector DNA strand is homologous to the sequence of the first terminus on said target DNA strand, and the sequence of the second homology arm on said vector DNA strand is homologous to the sequence of the second terminus on said target DNA strand; and b) subjecting the cell to conditions that allow intracellular homologous recombination to occur.

In another embodiment, a method is provided for making a recombinant DNA molecule comprising: a) introducing a double-stranded vector and first and second double-stranded oligonucleotides into a cell, said cell containing a double-stranded target DNA and expressing a bacterial recombinase, said vector comprising an origin of replication and two double-stranded homology arms, in the following order from 5' to 3' along a vector DNA strand: a first homology arm, the origin of replication, and a second homology arm; said target DNA comprising a target DNA sequence and two double-stranded termini, in the following order, from 3' to 5' along a target DNA strand: a first terminus, a target DNA sequence, and a second terminus; said first oligonucleotide comprising a first oligonucleotide DNA strand comprising, in the following order, from 3' to 5': a first nucleotide sequence and a second nucleotide sequence, said first nucleotide sequence being homologous to the nucleotide sequence of the first homology arm on said vector DNA strand, and said second nucleotide sequence being homologous to the nucleotide sequence of the first terminus on said target DNA strand; said second oligonucleotide comprising a second oligonucleotide strand comprising, in the following order, from 3' to 5', a third nucleotide sequence and a fourth nucleotide sequence, said third nucleotide sequence being homologous to the nucleotide sequence of the second homology arm on said vector DNA strand and said fourth nucleotide sequence being homologous to the nucleotide sequence of the second terminus on said target DNA strand; and b) subjecting the cell to conditions that allow intracellular homologous recombination to occur.

In another embodiment, a method is provided for making a recombinant DNA molecule comprising: a) introducing a double-stranded target DNA molecule into a cell, said cell containing a vector and expressing a bacterial recombinase, said target DNA comprising a target DNA sequence and two double-stranded termini, in the following order, from 3' to 5' along a target DNA strand: a first terminus, a target DNA sequence, and a second terminus; said vector comprising an origin of replication and two homology arms, in the following order from 5' to 3' along a vector DNA strand: a first homology arm, the origin of replication and a second homology arm; such that the sequence of the first homology arm on said vector DNA strand is homologous to the sequence of the first terminus on said target DNA strand, and the sequence of the second homology arm on said vector DNA strand is homologous to the sequence of the second terminus on said target DNA strand; and b) subjecting the cell to conditions that allow intracellular homologous recombination to occur.

In another embodiment, a method is provided for making a recombinant DNA molecule comprising: a) introducing a double-stranded target DNA molecule and a first and second double-stranded oligonucleotide into a cell, said cell containing a vector and expressing a bacterial recombinase, said target DNA comprising a target DNA sequence and two termin, in the following order, from 3' to 5' along a target DNA strand: a first terminus, a target DNA sequence, and a second terminus; said first oligonucleotide comprising a first oligonucleotide DNA strand comprising, in the following order, from 3' to 5': a first nucleotide sequence and a second nucleotide sequence, said first nucleotide sequence being homologous to the nucleotide sequence of the first homology arm on said vector DNA strand, and said second nucleotide sequence being homologous to the nucleotide sequence of the first terminus on said target DNA strand; said second oligonucleotide comprising a second oligonucleotide strand comprising, in the following order, from 3' to 5', a third nucleotide sequence and a fourth nucleotide sequence, said third nucleotide sequence being homologous to the nucleotide sequence of the second homology arm on said vector DNA strand and said fourth nucleotide sequence being homologous to the nucleotide sequence of the second terminus on said target DNA strand; and said vector comprising an origin of replication and two homology arms, in the following order from 5' to 3' along a vector DNA strand: a first homology arm, the origin of replication and a second homology arm; and b) subjecting the cell to conditions that allow intracellular homologous recombination to occur.

In another embodiment, a method is provided for making a recombinant DNA molecule comprising: a) introducing a double-stranded vector and a double-stranded target DNA into a cell expressing a bacterial recombinase, said vector comprising an origin of replication and two homology arms, in the following order from 5' to 3' along a vector DNA strand: a first homology arm, the origin of replication and a second homology arm, said target DNA comprising a target DNA sequence and two termini, in the following order, from 3' to 5' along a target DNA strand: a first terminus, a target DNA sequence; and a second terminus; such that the nucleotide sequence of the first homology arm on said vector DNA strand is homologous to the nucleotide sequence of the first terminus on said target DNA strand, and the nucleotide sequence of the second homology arm on said vector DNA strand is homologous to the sequence of the second terminus on said target DNA strand; and b) subjecting the cell to conditions that allow intracellular homologous recombination to occur.

In a specific embodiment, of this method the host cell further contains a nucleotide sequence encoding a site-specific recombinase operatively linked to a promoter, and the vector further comprises a first and second recognition site for the site-specific recombinase, a first recognition site located outside the first and second homology arms, and a second site-specific recombinase recognition site located inside the first and second homology arms; and during or after step b), inducing expression of the site-specific recombinase.

In another specific embodiment of this method, the host cell further contains a nucleotide sequence encoding a site-specific endonuclease operatively linked to a promoter, and the vector further comprises a recognition site for the site-specific endonuclease located inside the first and second homology arms; and during or after step b), inducing expression of the site-specific endonuclease.

In another embodiment, the inventions provides a method for making a recombinant DNA molecule comprising: a) introducing a double-stranded vector, a double-stranded target DNA molecule, and a first and second double-stranded oligonucleotide into a cell expressing a bacterial recombinase, said vector comprising an origin of replication and two double-stranded homology arms, in the following order from 5' to 3' along a vector DNA strand: a first homology arm, the origin of replication and a second homology arm; said target DNA comprising target DNA sequence and two double-stranded termini, in the following order, from 3' to 5' along a target DNA strand: a first terminus, a target DNA sequence, and a second terminus; said first oligonucleotide comprising a first oligonucleotide DNA strand comprising, in the following order, from 3' to 5': a first nucleotide sequence and a second nucleotide sequence, said first nucleotide sequence being homologous to the nucleotide sequence of the first homology arm on said vector DNA strand, and said second nucleotide sequence being homologous to the sequence of the first terminus on said target DNA strand; said second oligonucleotide comprising a second oligonucleotide strand comprising, in the following order, from 3' to 5', a third nucleotide sequence and a fourth nucleotide sequence, said third nucleotide sequence being homologous to the nucleotide sequence of the second homology arm on said vector DNA strand and said fourth nucleotide sequence being homologous to the nucleotide sequence of the second terminus on said target DNA strand; and b) subjecting the cell to conditions that allow intracellular homologous recombination to occur.

In a specific embodiment of this method, the host cell further contains a nucleotide sequence encoding a site-specific recombinase operatively linked to a promoter, and the vector further comprises a first and second recognition site for the site-specific recombinase, a first recognition site located outside the first and second homology arms, and a second site-specific recombinase recognition site located inside the first and second homology arms; and during or after step b), inducing expression of the site-specific recombinase.

In another specific embodiment of this method, wherein the host cell further contains a nucleotide sequence encoding a site-specific endonuclease operatively linked to a promoter, and the vector further comprises a recognition site for the site-specific endonuclease located inside the first and second homology arms; and during or after step b), inducing expression of the site-specific endonuclease.

In specific embodiments, the vector further comprises a selectable marker located outside the homology arms, such that the vector comprises, in either of the following two orders from 5' to 3' along a vector DNA strand: i) the first homology arm, the selectable marker, the origin of replication and the second homology arm, or ii) the first homology arm, the origin of replication, the selectable marker, and the second homology arm. In a specific embodiment, the selectable marker confers antibiotic resistance to the cell containing the vector.

In various specific embodiments, the bacterial recombinase is RecE/T or Redα/β recombinase or both RecE/T and Redα/β. In other specific embodiments, the cell is a bacterial cell. In other specific embodiments, the cell is an *E. coli* cell. In other specific embodiments, the cell eukaryotic cell that recombinantly expresses RecE/T and/or Redα/β protein. In other specific embodiments, the method further comprises isolating a recombinant DNA molecule that comprises the target DNA inserted into the vector.

In another embodiment, the invention provides a double-stranded DNA vector useful for directed cloning or subcloning of a target DNA molecule of interest, said vector comprising an origin of replication and two homology arms, in the following order from 5' to 3' along a vector DNA strand: a first homology arm, the origin of replication and a second homology arm; such that the nucleotide sequence of the first homology arm on a first vector DNA strand is homologous to the sequence of the first terminus on a first target DNA strand, and the nucleotide sequence of the second homology arm on the first vector DNA strand is homologous to the nucleotide sequence of the second terminus on the first target DNA strand. In a specific embodiment of the vector, the origin of replication is a bacterial origin of replication. In another specific embodiment, the origin of replication functions in *E. coli*. In another specific embodiment, the origin of replication functions in a mammalian cell.

The invention further provides a cell comprising a double-stranded DNA vector useful for directed cloning or subcloning of a target DNA molecule of interest, said vector comprising an origin of replication and two homology arms, in the following order from 5' to 3' along a vector DNA strand: a first homology arm, the origin of replication and a second homology arm; such that the nucleotide sequence of the first homology arm on a first vector DNA strand is homologous to the sequence of the first terminus on a first target DNA strand, and the nucleotide sequence of the second homology arm on the first vector DNA strand is homologous to the nucleotide sequence of the second terminus on the first target DNA strand. In a specific embodiment, the cell is a bacterial cell.

The invention further provides a kit useful for directed cloning or subcloning of a target DNA molecule comprising in one or more containers: a) a double-stranded DNA vector useful for directed cloning or subcloning of a target DNA molecule of interest, said vector comprising an origin of replication and two homology arms, in the following order from 5' to 3' along a vector DNA strand: a first homology arm, the origin of replication and a second homology arm; such that the nucleotide sequence of the first homology arm on a first vector DNA strand is homologous to the sequence of the first terminus on a first target DNA strand, and the nucleotide sequence of the second homology arm on the first vector DNA strand is homologous to the nucleotide sequence of the second terminus on the first target DNA strand; and b) a cell containing a bacterial recombinase. In a specific embodiment of the kit, the homology arms have sequence homology to a BAC, PAC, lambda, plasmid or YAC based cloning vector. In another specific embodiment of the kit, the first and second double-stranded oligonucleotide have nucleotide sequence homology to a BAC, PAC, lambda, plasmid or YAC based cloning vector.

In another embodiment, a kit useful for directed cloning or subcloning of a target DNA molecule is provided comprising in one or more containers: a) a double-stranded DNA vector useful for directed cloning and subcloning of a target DNA molecule of interest, said vector comprising an origin of replication and two homology arms, in the following order from 5' to 3' along a vector DNA strand: a first homology arm, the origin of replication and a second homology arm; b) a first double-stranded oligonucleotide comprising a first oligonucleotide DNA strand comprising, in the following order, from 3' to 5': a first sequence and a second sequence, said first nucleotide sequence being homologous to the nucleotide sequence of the first homology arm on said vector DNA strand, and said second nucleotide sequence being homologous to the nucleotide sequence of a first terminus on a target DNA strand; c) a second double-stranded oligonucleotide comprising a second oligonucleotide strand comprising, in the following order, from 3' to 5': a third nucleotide sequence and a fourth nucleotide sequence, said third nucleotide sequence being homologous to the nucleotide sequence of the second homology arm on said vector DNA strand and said fourth nucleotide sequence being homologous to the nucleotide sequence of a second terminus on said target DNA strand; and d) a cell containing a bacterial recombinase. In a specific embodiment of the kit, the cell is an *E. coli* cell. In another specific embodiment of the kit, the cell is a frozen cell competent for uptake of DNA.

In another embodiment, the invention provides a kit useful for directed cloning or subcloning of a target DNA molecule comprising in one or more containers: a) a double-stranded DNA vector useful for directed cloning and subcloning of a target DNA molecule of interest, said vector comprising an origin of replication and two homology arms, in the following order from 5' to 3' along a vector DNA strand: a first homology arm, the origin of replication and a second homology arm; b) a first double-stranded oligonucleotide comprising a first oligonucleotide DNA strand comprising, in the following order, from 3' to 5': a first nucleotide sequence and a second nucleotide sequence, said first nucleotide sequence being homologous to the nucleotide sequence of the first homology arm on said vector DNA strand, and said second nucleotide sequence being homologous to the nucleotide sequence of a first terminus on a target DNA strand; and c) a second double-stranded oligonucleotide comprising a second oligonucleotide strand comprising, in the following order, from 3' to 5: a third nucleotide sequence and a fourth nucleotide sequence, said third nucleotide sequence being homologous to the nucleotide sequence of the second homology arm on said vector DNA strand and said fourth sequence being homologous to the nucleotide sequence of a second terminus on said target DNA strand. In a specific embodiment of the kit, the DNA vector is purified. In another embodiment of the kit, the DNA vector, the first double-stranded oligonucleotide, and the second double-stranded oligonucleotide are purified.

In other specific embodiments of kits provided by the invention the target DNA molecule comprises bacterial, viral, parasite, or protozoan DNA. In other specific embodiments, the target DNA molecule comprises a genetic mutation or polymorphism known or suspected to be associated with a disorder or disease. In other specific embodiments, the bacterial recombinase is RecE/T or Recα/β recombinase or both RecE/T and Recα/β recombinases.

The methods of the invention may be used in diagnostics. For example, plasmids or linear DNA fragments may be designed to capture a specific DNA target to detect its presence in a sample from a subject e.g., a viral DNA present in a patient's sample. In one embodiment, the invention provides methods for detection of target DNA known or suspected to be associated with a disorder or disease when genetically mutated. In specific embodiments, the target DNA is a bacterial, viral, parasite, or protozoan DNA. In a specific embodiment, a method is provided which further comprise detecting a recombinant DNA molecule that comprises the target DNA inserted into the vector. In another embodiment, the method further comprises detecting a recombinant DNA molecule that comprises the target DNA inserted into the vector.

In another embodiment, the invention provides a method of detecting the presence of an infectious agent wherein the target DNA is derived from a patient suspected of having the infectious disease, and the sequences of the first and second homology arms are homologous to the sequences present in DNA of the infectious agent. In a specific embodiment, the target DNA is derived from a patient suspected of having the infectious disease, and said second and fourth nucleotide sequences are homologous to sequences present in DNA of the infectious agent. In other specific embodiments, the infectious agent is a virus, bacteria, protozoa, fungus, or parasite.

In another embodiment, a method is provided for detecting the presence of a genetic condition, disease, disorder, or polymorphic trait, wherein the target DNA is derived from a patient suspected of having a genetic condition, disease, disorder, or polymorphic trait, and the sequence of the first homology arm is homologous to the sequence upstream from a site known or suspected to be associated with the genetic condition, disease, disorder, or polymorphic trait, and the sequence of the second homology arm is homologous to the sequence downstream from a site known or suspected to be associated with the genetic condition, disease, disorder, or polymorphic trait. In a specific embodiment, a method is provided for detecting the presence of a genetic condition, genetic disease, genetic disorder, or polymorphic trait wherein the target DNA is derived from a patient suspected of having the genetic condition, genetic disease, genetic disorder, or polymorphic trait, and the sequence of the first double-stranded oligonucleotide is homologous to the sequence upstream from a site known or suspected to be associated with the genetic condition, genetic disease, genetic disorder, or polymorphic trait, and the sequence of the second double-stranded oligonucleotide is homologous to the sequence downstream from a site known or suspected to be associated with the genetic condition, genetic disease, genetic disorder, or polymorphic trait. In a specific embodiment, the genetic condition, genetic disease, genetic disorder, or polymorphic trait is or predisposes the patient to cancer, asthma, arthritis, drug resistance, drug toxicity, or a neural, neuropsychiatric, metabolic, muscular, cardiovascular, or skin condition, disease or disorder.

4. DESCRIPTION OF THE FIGURES

Figure 1B:
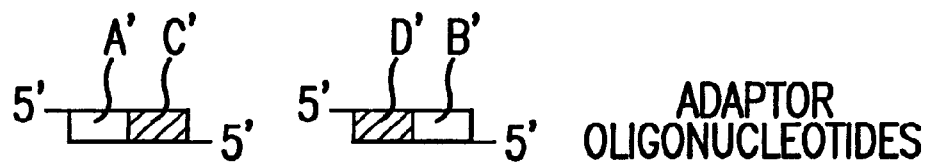
Figure 1C:
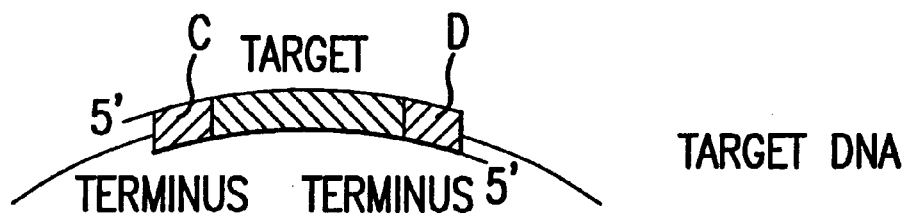

FIGS. 1A–C. Components of the homologous recombination cloning and subcloning methods.

- A. The vector, comprising an origin of replication (origin), a selectable marker (Sm), and two homology arms (labeled A and B).
- B. Optional double-stranded oligonucleotide adaptors. Each adaptor comprises a region of homology (labeled A' and B') to the homology arms (A and B, respectively); and a second region of homology (labeled C' and D') to a terminus of the target DNA (respectively labeled C and D).
- C. The target DNA. The terminal nucleotide sequences of the target DNA (C)and D) can either be homologous to nucleotide sequences of one of the homology arms of the vector (respectively labeled A and B), or to nucleotide sequences of the optional adaptor oligonucleotides (respectively labeled C' and D').

Figure 2:
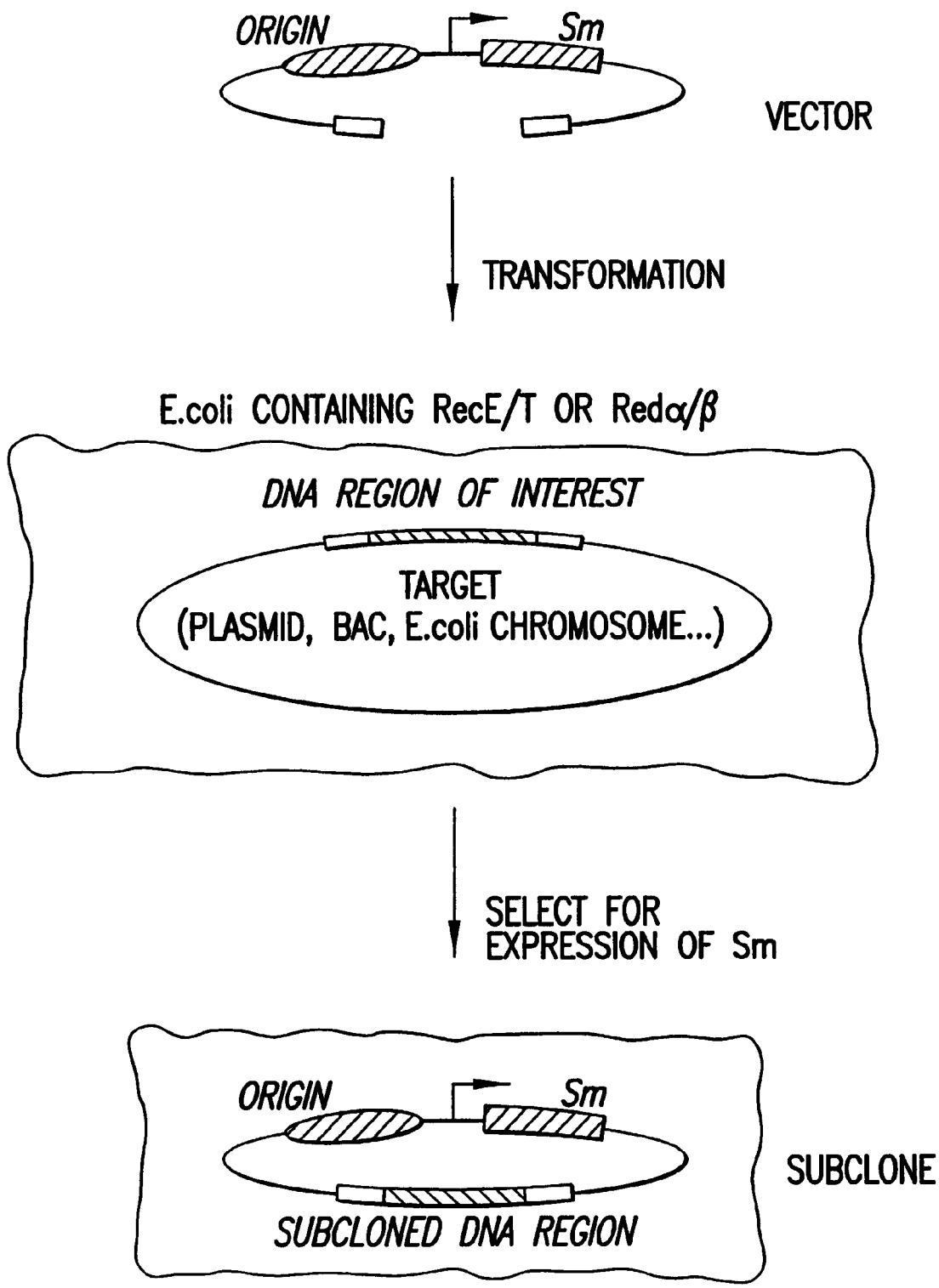

FIG. 2. Experimental outline of Approach 1. The vector for subcloning by homologous recombination is introduced, e.g., by transformation, into an *E. coli* host within which the target DNA and RecE/T or Redα/β proteins are already present. The diagram shows a linear DNA molecule carrying an *E. coli* replication origin, and a selectable marker gene (Sm), which is preferably a gene whose product confers resistance to an antibiotic, flanked by "homology arms". The homology arms, are shown as thick grey blocks at the ends of the linear DNA molecule, are short regions of sequence homologous to two regions in the target DNA that flank the DNA region to be subcloned, called target DNA termin, are shown as thick lines flanked by the homology arms. After transformation, selection for expression of the Sm gene is imposed to identify those cells that contain the product of homologous recombination between the homology arms of the linear DNA molecule and the target.

Figure 3:
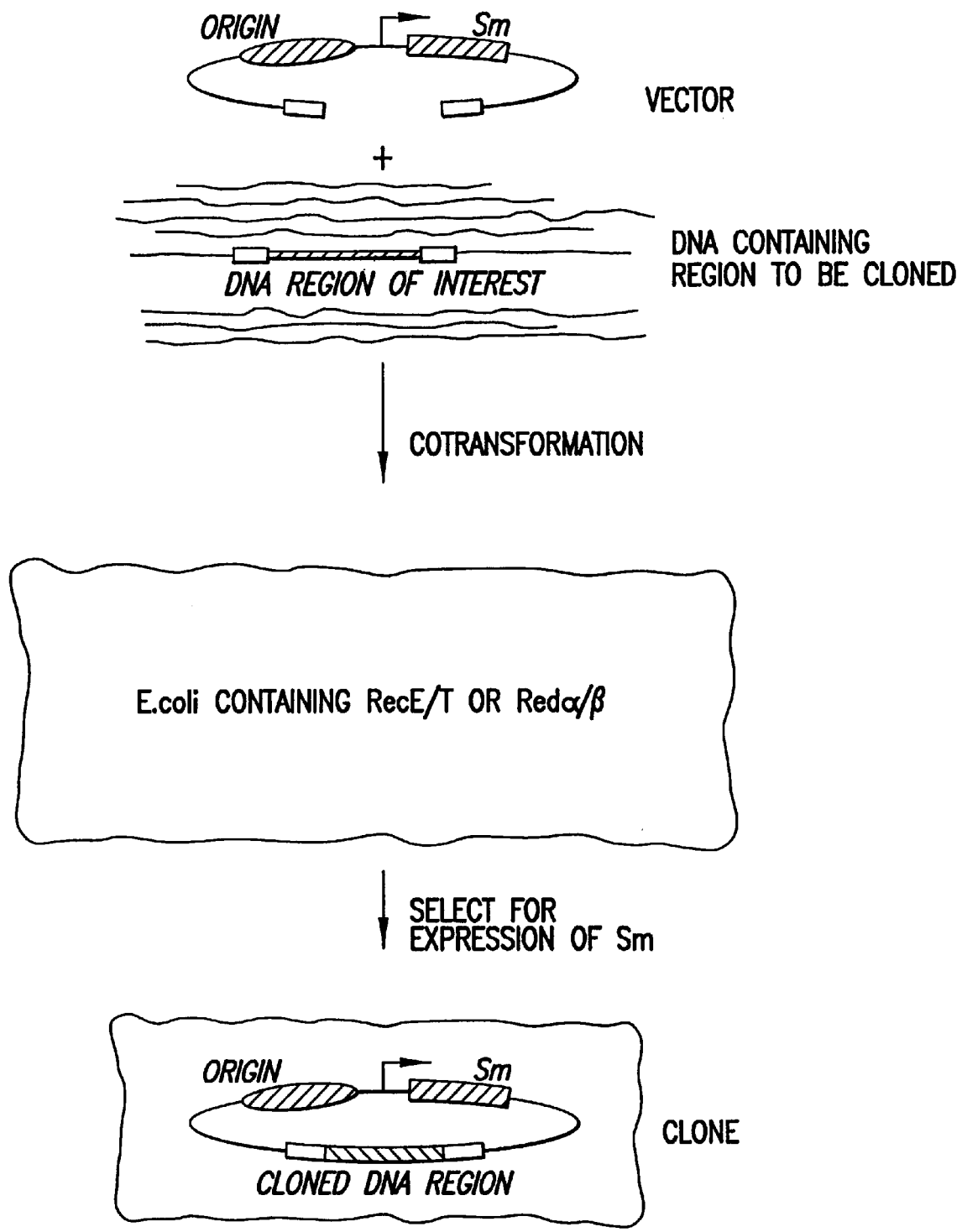

FIG. 3. Diagrammatic representation of Approach 2. The approach is similar to that used in FIG. 1, except in this case the target DNA molecule is not already present in the *E. coli* host, but, rather, is co-introduced with the linear DNA vector molecule. The target DNA can be any source, either, as illustrated, a mixture from which the DNA region of interest is cloned, or a highly enriched DNA molecule from which the DNA region is subcloned. As in FIG. 1, the homology arms are shown in thick grey blocks.

Figure 4:
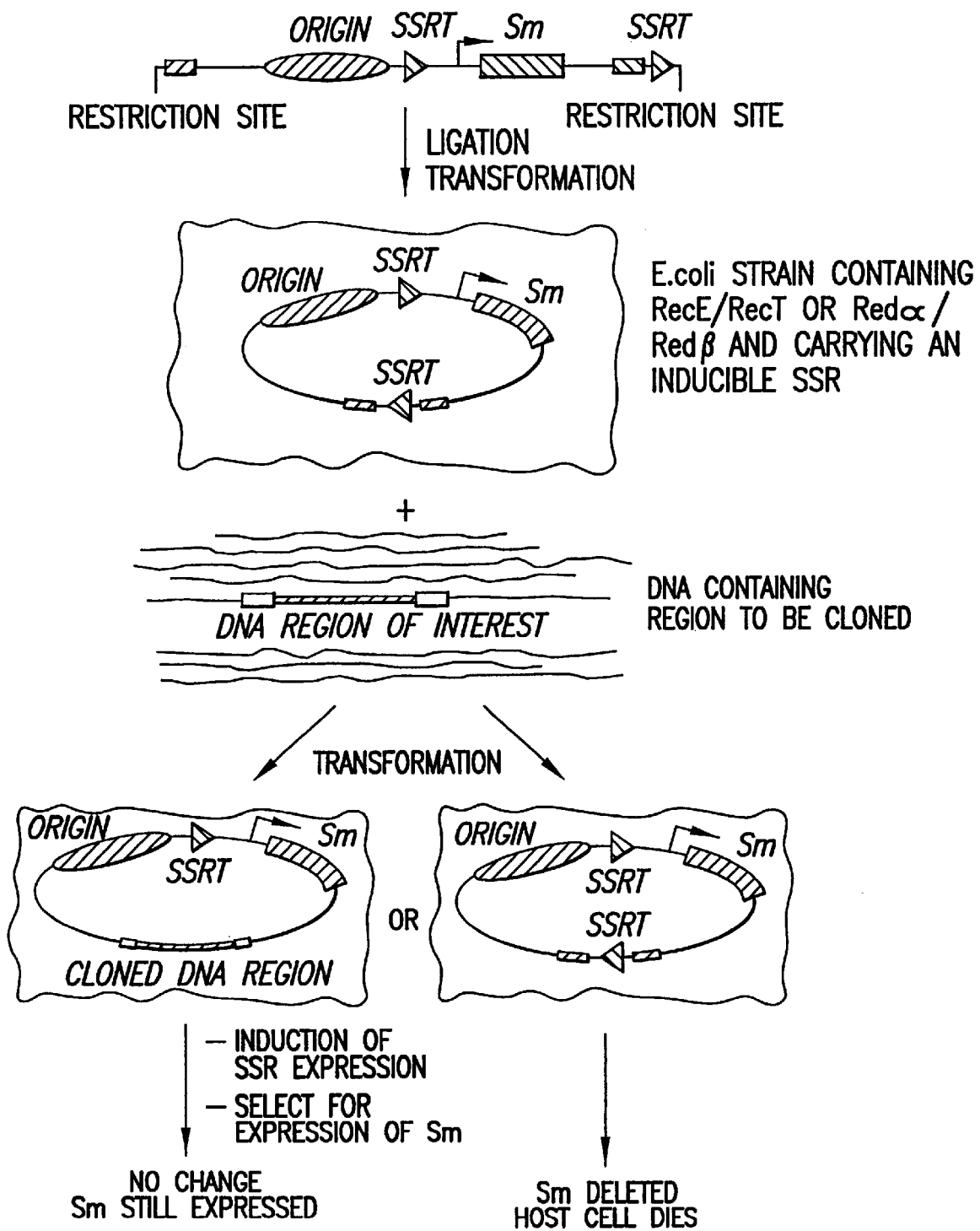

FIG. 4. Diagrammatic representation of an example of Approach 3. The cloning or subcloning vector includes an *E. coli* origin of replication and a selectable marker gene (Sm) flanked by two short homology arms, shown as thick grey blocks. Additionally, the vector includes two recombination target sites (SSRTs) one of which is between the origin and the selectable marker gene. Most simply, the vector is constructed first as a linear DNA fragment as shown in the figure. Upon circularization, the second SSRT is located between the homology arms oriented as a direct repeat with respect to the first SSRT, so that site-specific recombination between the two SSRTs results in the production of two different circular molecules, thereby separating the origin and the selectable marker gene. The circularized vector is transformed into an *E. coli* strain within which RecE/T or Redα/β proteins is expressed, or can be expressed. The *E. coli* strain also carries an inducible site-specific recombinase (SSR) gene, the product of which recognizes the SSRTs in the vector so that site-specific recombination between the SSRTs does not occur until the site-specific recombinase gene is induced for expression. The *E. coli* cells carrying the vector and the regulated site-specific recombinase gene are prepared so that they contain RecE/T or Redα/β proteins and are competent for transformation. DNA molecules containing the region to be cloned is then introduced into a host cell. After homologous recombination between the homology arms, expression of the site-specific recombinase protein is induced and selection for expression of the selectable marker gene is imposed. Before site-specific recombination, cells will contain either unrecombined vector carrying two SSRTs or the intended homologous recombination product which carries only one SSRT, since homologous recombination results in deletion of the SSRT located between the homology arms. After expression of the site-specific recombinase is induced, and selection for expression of the selectable marker is imposed, cells containing the product of homologous recombination will survive, since this product is no longer a substrate for site-specific recombination.

Figure 5:
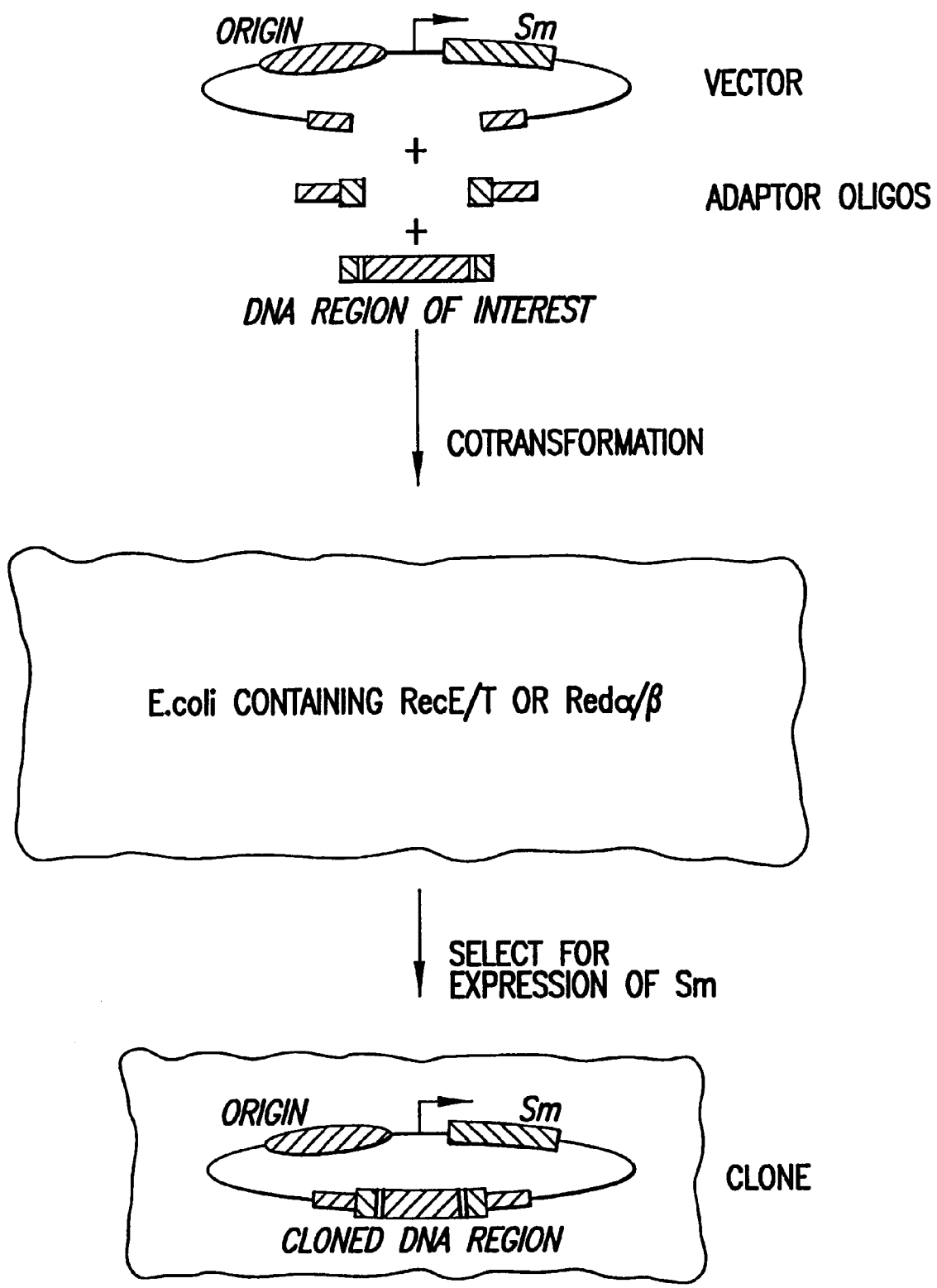

FIG. 5. Use of adaptor oligonucleotides for cloning and subcloning by RecE/T or Redα/β homologous recombination. The diagram illustrates a variation of Approach 2, shown in FIG. 3, above. Two adapter oligonucleotides each contain two regions of homology, one to one of the homology arms of the vector and a second region of homology to one of the two termini of the target DNA region of interest. Circularization of the vector and cloning of the DNA region of interest is accomplished by homologous recombination between the vector and the adapters and between the adapters and the target DNA. In this embodiment the vector and the target DNA do not share sequence homology. Thus, the same vector may be used to clone or subclone different target DNAs by using a target-specific adaptor oligonucleotides for each target DNA. Adapter oligonucleotides can also be used in the methods of Approaches 1 and 3, as outlined in FIGS. 1 and 3, above.

Figure 6:
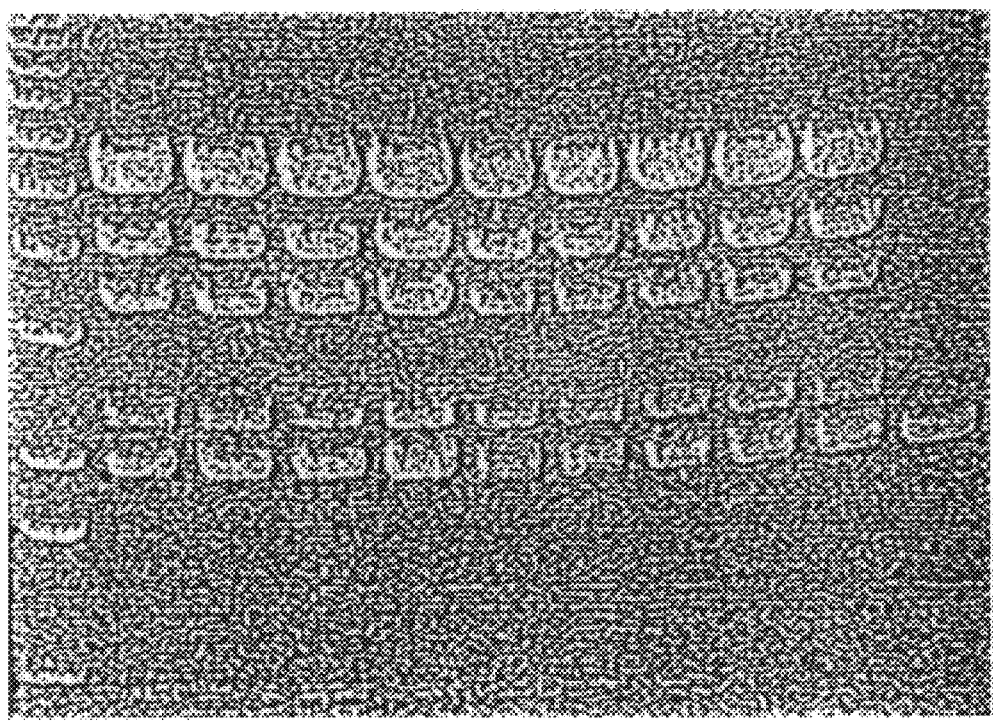

FIG. 6. An ethidium bromide stained agarose gel depicting DNA digested with EcoRI isolated from 9 independent colonies (lanes 1–9) obtained from the mAF4 BAC experiment. Lane M, 1 kb DNA size standards (BRL, Bethesda, Md.). Lane 10, EcoRI digestion of the starting vector. The experiment is described in detail in the Example in Section 6.

Figure 7A:
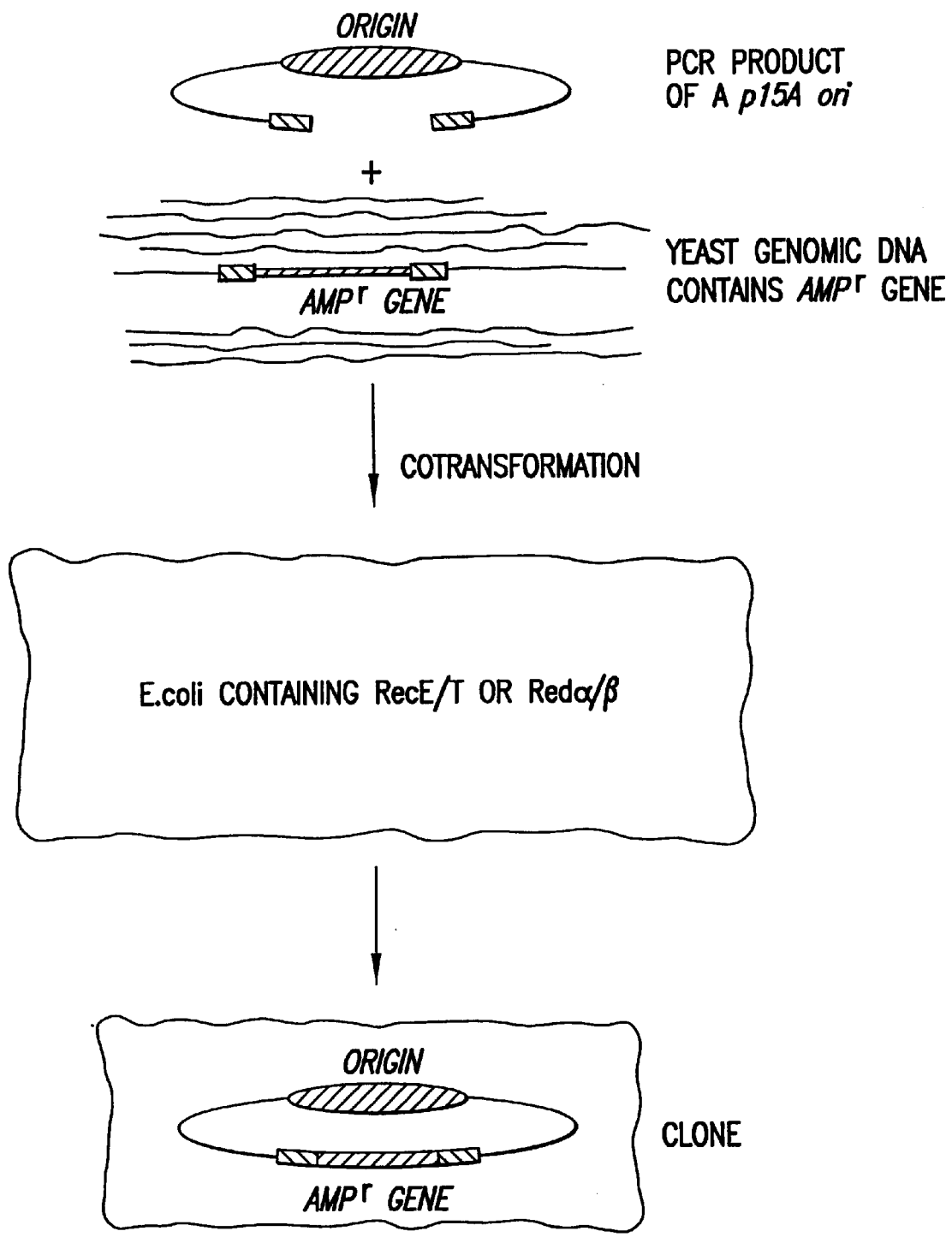
Figure 7B:
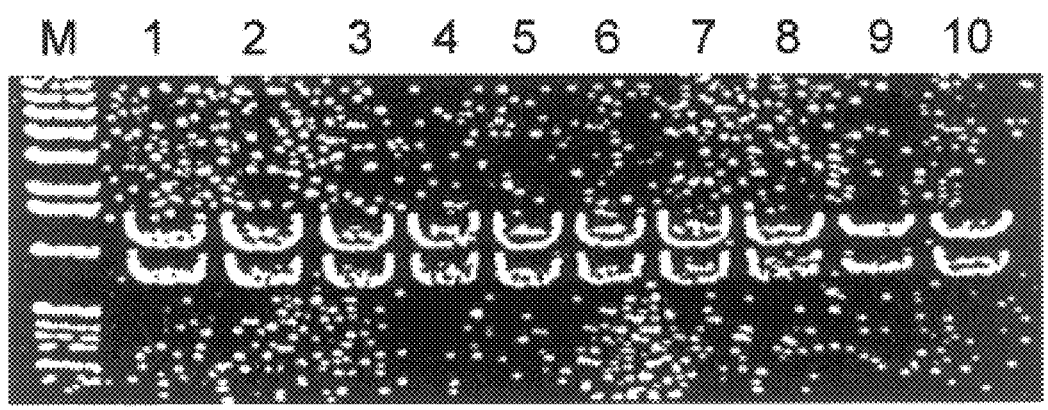

FIGS. 7A–B. Cloning of a DNA region from a total yeast genomic DNA. A. A PCR fragment made to amplify the p15A origin, and flanked by 98 or 102 bp homology arms to 98 or 102 bps either side of an integrated ampicillin resistance gene in the yeast strain, MGD 353-13D, is illustrated. The PCR product (0. 5 mg) was mixed with total yeast genomic DNA (4.0 mg) and coelectroporated into JC5519 *E. coli* containing Redα/β expressed from pBADαβγ. Clones were identified by selection for ampicillin resistance. B. An ethidium bromide stained gel to confirm the correct products from 10 chosen colonies.

5. DETAILED DESCRIPTION OF THE INVENTION

The present invention is directed to methods and compositions for DNA cloning and subcloning using bacterial recombinase-mediated homologous recombination. The inventor has discovered that bacterial recombinases may be utilized in a particular manner to achieve high-efficiency targeted cloning and subcloning.

Preferably, the bacterial recombinase used is RecE/T and/or Redα/β. The RecE/T pathway in *E. coli* has been described previously and its components have been partially characterized (Hall and Kolodner, 1994, supra; Gillen et al., 1981, supra). Recombination via the RecE/T pathway requires the expression of two genes, recE and recT, the DNA sequences of which have been published (Hall et al., 1993, J. Bacteriol. 175:277–278). The RecE protein is functionally similar to λ exo, which is also called Redα, and the RecT protein is functionally similar to Redβ and erf of phage P22 (Gillen et al., 1977, J. Mol. Biol. 113:27–41; Little, 1967, J. Biol. Chem. 242:679–686; Radding and Carter, 1971, J. Biol. Chem. 246:2513–2518; Joseph and Kolodner, 1983, Biol. Chem. 258:10411–17; Joseph and Kolodner, 1983, Biol. Chem. 258:10418–24; Muniyappa and Radding, 1986, J. Biol. Chem. 261:7472–7478; Kmiec and Hollomon, 1981, J. Biol. Chem. 256:12636–12639; Poteete and Fenton, 1983, J. Mol. Biol. 163: 257–275; Passy et al., 1999, Proc. Natl. Acad. Sci. USA 96:4279–4284, and references cited therein). Described herein are methods and compositions relating to the use of bacterial recombinases for directed DNA cloning and subcloning. As used herein, the term "DNA cloning" refers to the process of inserting DNA from any source into an autonomously replicating vector so that it can be propagated in the host cell. The term "DNA subcloning" refers to the process of shuttling of DNA fragments already present in an autonomously replicating vector into another autonomously replicating vector, or shuttling DNA fragments from a highly enriched DNA molecule, such as a purified viral genome or a DNA fragment previously amplified by PCR, into an autonomously replicating vector. The term "directed" or "targeted" cloning and subcloning refers to the use of homology arms and, in various embodiments, adaptor oligonucleotides, to select a target DNA, and to direct the orientation of the insertion of the target DNA by the choice and the orientation of the homology arms. It should be noted that all applications of the methods of present invention apply to methods for both cloning and subcloning DNA.

The construction of the compositions and methods of the invention are described in detail herein. In particular, Section 5.1 describes mediated recombination cloning methods of the invention for targeted cloning of DNA fragments by homologous recombination. Section 5.2, below, describes compositions of the invention, including DNA constructs designed to target, capture and clone target DNA fragments of interest. Also described are nucleic acid molecules encoding bacterial recombinases such as RecE/T and/or Redα/β proteins, cells comprising such compositions, and the methods for constructing such nucleic acids and cells. Section 5.3, below, describes the use of bacterial recombinase-targeted cloning methods and kits for detection of gene expression and diagnosis of disease conditions.

5.1 Methods for Cloning and Subcloning by Homologous Recombination

The various methods described herein can be used for efficient and targeted cloning of any DNA of interest by bacterial recombinase-mediated homologous recombination. The three approaches described herein have as common components a cell expressing bacterial recombinase recombination proteins, and a vector. An example of the vector is shown in FIG. 1A. The vector comprises three essential elements: an origin of replication and two short regions of double-stranded DNA, herein called 'homology arms'. The homology arms are specifically designed to allow the vector to 'capture' a target DNA of interest between the homology arms by homologous recombination. The sequence, position, and orientation of the homology arms are important for correct insertion of the target DNA between the arms. In one embodiment, where the homology arms have sequence homology to the termini of target DNA, the two homology arms correspond in sequence to DNA flanking the target DNA of interest, one arm (indicated as A in FIG. 1) corresponding to a DNA sequence upstream from the target DNA (indicated as C in FIG. 1) and the second arm (indicated as B in FIG. 1) corresponding to a sequence located downstream from the target DNA (indicated as D in FIG. 1). The orientation of the two arms relative to the desired insert must be the same as is the orientation of the homologous sequence relative to the target DNA (see FIG. 1), such that recombination between the homology arms and the target DNA results in the target DNA being inserted between, or 'inside' (see FIG. 1), the two homology arms. As used herein, a position is defined as being 'inside' the homology arms if it is positioned between the two homology arms, such that a first homology arm is between the origin of replication and itself in one direction, and a second homology arm is positioned between the origin of replication and itself in the other direction. On the other hand, a position is defined as being "outside" the homology arms if, in one direction, neither homology arm separates itself from the origin of replication. Thus, by definition, the replication origin and the selectable marker are located on the vector 'outside' the homology arms (see FIG. 1), so that insertion of the target sequence preserves the origin of replication and the selectable marker on the plasmid. On the other hand, the target DNA is, by definition, inserted 'inside' the homology arms. FIG. IA depicts pictorially the meaning of 'inside' and 'outside' of the homology arms.

In an alternative embodiment, the homology arms have sequence homology to a set of double-stranded adaptor oligonucleotides. Such adapter oligonucleotides are illustrated in FIG. 1B. The sequence of each adaptor oligonucleotide comprises the sequence of one of the homology arms of the vector, and additionally, a sequence homologous to a sequence that flanks the target gene of interest (see FIG. 1C). Thus, one adaptor oligonucleotide contains homology to DNA sequence of one homology arm (indicated as A' in FIG. 1), and a nucleotide sequence upstream from the target DNA (indicated as C' in FIG. 1). The second adaptor oligonucleotide contains homology to a DNA sequence of one homology arm (indicated as B' in FIG. 1), as well as a nucleotide sequence located downstream from the target DNA (indicated as D' in FIG. 1). In this way, adaptor oligonucleotides may be used to adapt a generic homology cloning vector to target a specific gene sequence of interest by varying the sequence of the adaptor oligonucleotide (see FIG. 5). The methods and compositions that can be used to carry out the various embodiments of the invention are described in detail herein.

The methods described below include three alternative approaches to directed cloning by homologous recombination. As described in detail below, each of the three approaches has its own advantages that make it preferred for a particular cloning application. These methods and applications are described in detail below. In one approach, depicted in FIG. 2, the cloning vehicle is introduced into a cell that contains the target DNA of interest. This first approach may be used to conveniently shuttle an insert from one replicon to another, without the need for cumbersome restriction analysis and in vitro manipulations. This approach is useful for applications in which the target DNA already exists in an *E. coli* replicon and its further use requires the subcloning of a chosen part. For example, the use of a DNA clone isolated from a cosmid, phage or BAC library is facilitated by subcloning chosen portions into a new vector in order to sequence the insert or to express the protein encoded by the gene. In a second approach, depicted in FIG. 3, the cloning vector and the target DNA of interest are prepared and then added together into a cell. Alternatively, as shown in FIG. 4, the DNA of interest can be added to a cell that already contains the cloning vector. The latter two approaches are useful for applications in which the target DNA is derived from any external source, such as, for example, DNA derived from a cancer cell.

5.1.1 Approach 1: Introduction of Vector into Host Cell Containing Target DNA

In one embodiment, as depicted in FIG. 2, the target DNA sequence is already present within a host cell that expresses a bacterial recombinase. For example, the target DNA may reside on an independently replicating DNA molecule, such as, but not limited to, a plasmid, a phage, bacterial artificial chromosome (BAC) or the *E. coli* chromosome in an *E. coli* host cell. Methods for constructing host cells that express a bacterial recombinase such as RecE/T or Redα/β recombinase are described in detail in Section 5.2.2.

The vector DNA, comprising an origin of replication and two homology arms located on either side of the origin and the marker, is introduced into the host cell. Preferably, the vector is a linear molecule and the homology arms are located at the respective ends of the linear molecule, although they may be internal. After entry into the cell, homologous recombination between the homology arms of the vector DNA and the target sequences results in insertion of target DNA between the homology arms, and the resultant formation of a circular episome. Cells are then plated on selective media to select for the selective marker present on the vector. Since only circularized molecules are capable of replicating and being selected for in the host cell, many of the cells that grow on selective media will contain recombined molecules including the target DNA. In one embodiment, the ends of the linear vector DNA fragment may be blocked with modified nucleotides, to reduce the number of events produced by joining of the ends of the linear fragments by any means other than homologous recombination, i.e, illegitimate recombination. Such modified nucleotides, e.g., phosphothionate nucleotides, may be incorporated into the 5'-end nucleotide of the homology arm. Modified nucleotides may be incorporated during oligonucleotide synthesis of a primer used to construct the vector (see Section 5.2.1, below), or, alternatively, may be added by enzymatic or chemical modification of the oligonucleotide or linear vector DNA after synthesis. Methods for such modification of oligonucleotides and linear DNA fragments are well known in the art, and are described in detail in Section 5.2.2, below.

5.1.2 Approach 2: Co-Introduction of Vector and Target DNA into the Host Cell

In another embodiment, as depicted in FIG. 3, the vector DNA and the target DNA are mixed in vitro and co-introduced into a cell containing the RecE/T or Redα/β recombinases. The target DNA may be derived from any source. For example, the target DNA can be obtained from a biological sample, such as, but not limited to, whole blood, plasma, serum, skin, saliva, urine, lymph fluid, cells obtained from biopsy aspirate, tissue culture cells, media, or non-biological samples such as food, water, or other material. Methods for preparation of DNA from such sources are well known to those of skill in the art (see, e.g., Current Protocols in Molecular Biology series of laboratory technique manuals, 1987–1994 Current Protocols, 1994–1997 John Wiley and Sons, Inc.).

The vector and the target DNA are prepared, mixed in vitro, and then co-introduced into cells expressing bacterial recombinase proteins, preferably by transformation in *E. coli* by co-electroporation. The vector DNA may be in the form of linear DNA or a circular plasmid DNA. In a preferred embodiment, the vector is a linear DNA molecule. The source of target DNA is mixed in weight excess to, or excess, relative to the vector DNA, in order to introduce as many copies of the target DNA region of interest into the cell as possible, thereby maximizing the yield of recombinant products. Cells are grown in selective media to select for circularized products. In a preferred embodiment the vector contains an antibiotic resistance marker, and cells are grown in the presence of antibiotic. Colonies that are capable of growth under such selection will contain circularized, recombined forms of the linear fragment.

In one embodiment, the ends of the linear vector DNA fragment may be blocked with modified nucleotides, as described below in Section 5.2.1. Methods for such modification of oligonucleotides are well known in the art, as described below in Section 5.2.2.

This approach is particularly useful where the target DNA is obtained from a source external to *E. coli,* such as yeast or eukaryotic cells. In one embodiment, this method may be used for diagnostic purposes to detect the presence of a particular DNA in any biological specimen. For example, the method may be used to detect the presence of a specific estrogen receptor or BRCA 1 allele in a biopsy sample extracted from a breast cancer patient.

In another embodiment, the method may be used to amplify regions of DNA as an alternative to amplification by polymerase chain reaction (PCR) techniques. Amplification by homologous recombination, cloning and propagation in *E. coli* offers several advantages over PCR-based techniques. First, PCR error can be a substantial drawback for many purposes. Combinations of pairs of PCR primers tend to generate spurious reaction products. Moreover, the number of errors in the final reaction product increases exponentially with the each round of PCR amplification after an error is introduced into a DNA sample. On the other hand, amplification by homologous recombination cloning has the advantage of the cellular proofreading machinery in *E. coli* and is thus at least 1000 times more faithful. Second, there are fewer restrictions on the size of the DNA region that may be amplified using the present method. Amplification of DNA regions longer than a few kilobases (greater than 5–10 kb) is difficult using PCR techniques. The present method is suitable for cloning much larger regions, at least to approximately one hundred kilobases. At present, cloning a genome involves the tedious processes of creating a large, random library followed by sorting through and ordering individual clones. Using this method, homology arms can be designed and vectors constructed to direct the cloning of a genome into large, non-redundant, contiguous clones, called 'contigs'. Third, even after DNA is produced by a PCR technique, the PCR products need to be cloned in an extra processing step. Homologous recombination cloning techniques obviates the need for the extra subcloning step. The region of DNA that is to be amplified is simply inserted between homology arms and transformed with the vector DNA into a E. coli host.

The homologous recombination in this embodiment may be carried out in vitro, before addition of the DNA to the cells. For example, isolated RecE and RecT, or cell extracts containing RecE/T may be added to the mixture of DNAs. When the recombination occurs in vitro the selection of DNA molecules may be accomplished by transforming the recombination mixture in a suitable host cell and selecting for positive clones as described above.

5.1.3 Approach 3: Introduction of Target DNA into Host Cells Containing Vector DNA In another embodiment, target DNA is introduced into a cell which already contains vector DNA. Target DNA may be from any source, as described in 5.1.2 above, and may be either linear or circular in form. As described above, once the target DNA is inside the cell, homologous recombination between the homology arms and the target DNA results in the insertion of the target DNA between the homology arms. However, in this case, counter-selection is needed to select against unrecombined vector since both the desired product and the unrecombined vector expresses the selectable marker gene. Various embodiments are described in detail herein to accomplish this counter-selection. In one embodiment, for example, a method that utilizes a site-specific recombination and excision reaction can be used. This approach is depicted in FIG. 5. In another embodiment, an inducible nuclease is induced that cleaves the unrecombined vector. In both embodiments, the vectors that do not contain recombination products are eliminated.

The vector is first constructed as a plasmid, then introduced into the host cell, where it can be propagated. As shown in FIG. 5, the vector contains (i) an origin of replication (any origin); (ii) a selectable marker (Sm); (iii) the two homology arms; and (iv) a counter-selectable marker, such as, but not limited to, a pair of recognition for a site-specific recombinase, a first recognition site located outside the homology arms and a second recognition site located inside the homology arms, or a recognition site for an endonuclease, which can be used to select against the starting plasmid vector. As used herein, a site is located 'inside' the homology arms if it is positioned between the two homology arms, such that a first homology arm is between the origin of replication and itself in one direction, and a second homology arm is positioned between the origin of replication and itself in the other direction. On the other hand, a position is defined as being 'outside' the homology arms if, in one direction, neither homology arm separates itself from the origin of replication. (See FIG. 1 for a pictorial representation of the meaning of 'inside' versus 'outside' the homology arms.) The origin of replication and the selectable marker must be located outside the homology arms, as described in Section 5.1 above, such that insertion of the target sequence preserves the origin of replication and the selectable marker on the plasmid. The counter-selectable marker, endonuclease site or one of two site-specific recombinase target sites is preferably located 'inside' the homology arms (see FIG. 5), on the other side of the origin of replication and the selectable marker.

Any method known in the art that allows for counter-selection against the non-recombined vector can be used. For example, in one embodiment, counter-selection can be accomplished by an inducible site-specific recombinase (SSR). Site-specific recombinases are enzymes that recognize two target sites, called site-specific recombinase target sites (SSRTs), and act at these sites to mediate a DNA strand exchange and excision reaction (Halle, et al., FEMS Microbiol. Rev., 1997, 21:157–78; Sauer, 1994, Curr Opin Biotechnol. 5:521–7; Stark et al., 1992, Trends Genet., 8:432–9). Examples of site-specific recombinases are known in the art, including, but not limited to Cre, Flp, Kw, or R recombinases (Nunes-Dueby et al., 1998, Nucleic Acids Res. 26:391–406; Ringrose et al., 1997, Eur. J. Biochem. 248: 903–912; Utatsu et al., 1987, J. Bacteriol. 169: 55537–5545). When two directly repeated SSRTs reside on a circular plasmid, site-specific recombination between the two SSRTs results in the formation of two circular plasmids. Only the product containing the origin of replication is maintained in the cell. Thus, site-specific recombination between two directly repeated SSRTs in a circular plasmid results in deletion of the DNA sequence located between the two SSRTs on the side that does not include the origin of replication.

A DNA vector is constructed containing two SSRTs, oriented as direct repeats, one positioned inside the homology arms, and a second positioned outside the arms and between the selectable marker (SM) and the origin of replication. Recombination between SSRTs positioned in this way results in separation of the origin of replication from the selectable marker (see FIG. 5). Thus, the SSR will act on non-recombined DNA vectors, which contain two SSRTs, resulting in the loss of such plasmids from the host cell.

Host cells are then transformed with vector DNA by standard methods. In this embodiment the host cell must contain: 1) RecE/T and/or Redα/β genes and 2) a gene encoding an SSR. Preferably, the expression of RecE/T and/or Redα/β genes is inducible, but constitutive expression is also possible. The gene encoding a site-specific recombinase (SSR) that recognizes the SSRTs must be inducible. Inducible and constitutive promoters are well known in the art; methods for their use in construction and expression of recombinant genes are described in Section 5.2.3, below. If the RecE/T and/or Redα/β genes require induction for expression, the vector containing cells are grown under conditions to induce expression immediately before competent cells are prepared. Host cells containing vector DNA are selected for and maintained by plating and growing in selective media.

Competent cells are then prepared from the host cells containing the vector. Cells are transformed with the target DNA, which can be prepared from any source, e.g. total genomic DNA prepared from any cell. The cells are cultured briefly, to allow homologous recombination to occur. Homologous recombination results in deletion of the sequence between the homology arms containing one SSRT, and the insertion of the target gene sequence. The expression of the SSR is then induced. The SSR will act on the directly repeated SSRTs in the un-recombined vector, separating the selectable marker from the plasmid origin of replication. Plasmids containing insert targets have only one SSRT and remain intact. Selection may or may not be maintained throughout this step, but does need to be imposed soon after induction of the SSR, i.e., soon after the site-specific recombination takes place. In this way, induction of the SSR results in selecting for plasmids containing insert target genes.

In an alternative embodiment, an endonuclease can be used to linearize the vector between the homology arms in vivo, either just before, during, or after homologous recombination. Linearization of the vector before recombination will select for correct recombination products, since a linear plasmid will not survive in the cell unless it becomes circularized. After the recombination, the continued activity of the endonuclease will help select for plasmids containing inserts because during homologous recombination the SSR deletes the endonuclease recognition site and inserts the target DNA in its place. Since the endonuclease will cleave only non-recombined vectors, leaving plasmids with inserted target sequences intact, the continued activity of the endonuclease after recombination, selects against non-recombined products. For this embodiment, an endonuclease with a very rare recognition site must be used, so that no other sites will be present in the host cell DNA. Examples of such 'rare-cutters' are known in the art, including, but not limited to, the lambda cos, yeast HO or an intron-encoded endonuclease such as PI-SceI. The recognition site for the endonuclease should be cloned between the two homology arms, so that enzymatic digestion by the endonuclease results in linearization of the vector between the homology arms. The expression of the endonuclease gene must be inducible. Constructs and methods for inducible protein expression are discussed below, in Section 5.2.3.

In another embodiment, an SSR, for example, the Cre recombinase can be used, instead of an endonuclease, to linearize the unrecombined vector in vivo (see Mullins et al., 1997, Nucleic Acids Res.25:2539–40). In this case, the vector is constructed with only one SSRT site located inside the homology arms. An excess of oligonucleotide containing a copy of the same SSRT is oligonucleotide is mixed with the target DNA and co-transformed into the host with the target DNA. Preferably, the oligonucleotide is a short double-stranded DNA molecule. Where one of the recombining molecules has an SSRT residing on a short oligonucleotide, the site-specific recombinase will linearize the vector at its SSRT (Mullins et al, 1997, supra).

In another embodiment, the site-specific recombination and endonuclease approaches described above can be combined. In this case, the unrecombined vector is made to contain both an SSRT and an endonuclease site inside the homology arms. In one embodiment of this approach, the SSR and the endonuclease could be co-regulated under the control of a single inducible promoter. Constructs and methods for such co-regulated, inducible expression of proteins in discussed in Section 5.2.3, below.

In another embodiment, a combination of these uses of site-specific recombination for counter-selection can be employed. In this embodiment, two pairs of SSR/SSRTs are employed, for example Cre/lox and Flp/FRT. The vector contains two sites for the first SSR, SSR1, one located inside the homology arms, and the second located outside the homology arms, between the origin of replication and the selectable marker. In addition, the vector contains a site for the second SSR, SSR2, located inside the homology arms. Another site for SSR2 is located on short double-stranded oligonucleotides and are added along with target DNA during cell transformation, at an amount in excess to the target DNA. In a specific embodiment, for example, one SSR/SSRT pair for the linearization step is Cre/loxP and the second one for the deletion step is Flp/FRT.

In another embodiment, a direct counter-selection against the cell may be used. In this case the plasmid origin of replication directs single-copy (or very low copy) maintenance in E. coli. Origins of replication of this class include the iteron-class of origins such as the phage P1 origin, and plasmids based on the E. coli chromosomal origin, oriC. For suitable origins of replication, see Helinski, D. R, Toukdarian, A. E., Novick, R. P. Chapter 122, pp 2295–2324 in "Escherichia coli and Salmonella, Cellular and Molecular Biology" $2^{nd}$ edition Frederick C. Niedhardt, Ed. ASM Press, Washington, 1996, ISBN 1-55581-084-5. In this case, the vector can be constructed without any SSRTs, rather a counter-selectable gene is included between the homology arms. Such counter-selectable marker genes are known in the art, for example, the sacB, ccdB or tetracycline resistant genes may be used (see also, Reyrat et al., 1998, Infect. Immun. 66:4011–7 for a listing of suitable counter-selectable genes and methods). The intended homologous recombination reaction will delete the counter-selectable gene so that cells carrying the intended recombination product will survive under counter-selection pressure, whereas cells carrying the unrecombined vector will be killed.

5.2 Compositions for Cloning and Subcloning by Homologous Recombination

Compositions for cloning by homologous recombination in the various embodiments are described herein. For each of the cloning methods described in Section 5.2 below, three components are required to coexist in a single cell: first, a vector carrying two short regions of DNA (herein called 'homology arms'), having sequence homology to a target sequence; second, RecE/T and/or Redα/β protein pairs or other bacterial recombinase; and third, the target DNA sequence. Recombination between these homologous sequences present on the homology arms and the flanking regions of the target gene, mediated by a bacterial recombinase, results in the target DNA being inserted or 'captured' between the two homology arms. The compositions and the methods for their construction are described in detail herein.

5.2.1 The Homology Cloning Vector

The homology cloning vector may be a linear or circular DNA vector comprising an origin of replication, a selectable marker, and two short regions of DNA designed to capture a target DNA of interest. Several forms of cloning vehicles are possible, depending on the approach or method to be used. The preferred forms and methods for their construction are depicted in FIGS. 1–5, and described in detail herein.

5.2.1.1 the Origin of Replication

The vector requires an origin of replication, which is needed for replication and propagation of the plasmid. For cloning and propagation in E. coli, any E. coli origin of replication may be used, examples of which are well-known in the art (see, Miller, 1992, A Short Course in Bacterial Genetics, Cold Spring Harbor Laboratory Press, NY, and references therein). Non-limiting examples of readily available plasmid origins of replication are ColE1-derived origins of replication (Bolivar et al., 1977, Gene 2:95–113; see Sambrook et al., 1989, supra), p1SA origins present on plasmids such as pACYC184 (Chang and Cohen, 1978, J. Bacteriol. 134:1141–56; see also Miller, 1992, p. 10.4–10.11), and pSC101 origin available for low-copy plasmids expression are all well known in the art.

For example, in one embodiment, the origin of replication from a high-copy plasmid is used, such as a plasmid containing a ColE1-derived origin of replication, examples of which are well known in the art (see Sambrook et al., 1989, supra; see also Miller, 1992, A Short Course in Bacterial Genetics, Cold Spring Harbor Laboratory Press, NY, and references therein). One example is an origin from pUC19 and its derivatives (Yanisch-Perron et al., 1985, Gene 33:103–119). pUC vectors exist at levels of 300–500 copies per cell and have convenient cloning sites for insertion of foreign genes. For very high expression, λ vectors, such as λgt11 (Huynh et al., 1984, in "DNA Cloning Techniques:, Vol I: A Practical Approach", D. Glover, ed., pp 49–78, IRL Press, Oxford), or the T7 or SP6 phage promoters in cells containing T7 and Sp6 polymerase expression systems (Studier et al., 1990, Methods Enzymol., 185:60–89) can be used. When a lower level of expression is desired, an origin of replication from a medium or a low-copy may be used. Medium-copy plasmids are well known in the art, such as pBR322, which has a ColE1 derived origin of replication and 20–100 copies per cell (Bolivar et al, 1977, Gene 2:95–113; see Sambrook et al, 1989, supra), or pACYC184, one of the pACYC100 series of plasmids, which have a p15A origin of replication and exist at 30 10–12 copies per cell (Chang and Cohen, 1978, J. Bacteriol. 134:1141–56; see also Miller, 1992, p. 10.4–10.11). Low-copy plasmids are also well known in the art, for example, pSC101, which has a pSC 101 origin, and approximately 5 copies per cell. Both pACYC and pSC101 plasmid vectors have convenient cloning sites and can co-exist in the same cell as pBR and pUC plasmids, since they have compatible origins of replication and unique selective antibiotic markers. Other suitable plasmid origins of replication include lambda or phage P1 replicon based plasmids, for example the Lorist series (Gibson et al., 1987, Gene 53: 283–286).

When even less expression is desired, the origin of replication may be obtained from the bacterial chromosome (see Miller, 1992, supra; Niedhardt, F. C., ed., 1987, *Escherichia coli and Salmonella typhimurium*, American Society for Microbiology, Washington, D.C.; Yarmolinsky, M. B. & Stemberg, N., 1988, pp. 291–438, in Vol. 1 of *The Bacteriophages*, R. Calendar, ed., Plenum Press, New York). In addition, synthetic origins of replication may be used.

5.2.1.2 the Selectable Marker

To maintain the plasmid vector in the cell, the vector typically contains a selectable marker. Any selectable marker known in the art can be used. For construction of an *E. coli* vector, any gene that conveys resistance to any antibiotic effective in *E. coli*, or any gene that conveys a readily identifiable or selectable phenotypic change can be used. Preferably, antibiotic resistance markers are used, such as the kanamycin resistance gene ski from TN903 (Friedrich & Soriano, 1991, Genes. Dev. 5:1513–1523), or genes that confer resistance to other aminoglycosides (including but not limited to dihydrostreptomycin, gentamycin, neomycin, paromycin and streptomycin), the β-lactamase gene from IS1, that confers resistance to penicillins (including but not limited to ampicillin, carbenicillin, methicillin, penicillin N, penicillin O and penicillin V). Other selectable genes sequences including, but not limited to gene sequences encoding polypeptides which confer zeocin resistance (Hegedus et al. 1998, Gene 207:241–249). Other antibiotics that can be utilized are genes that confer resistance to amphenicols, such as chloramphenicol, for example, the coding sequence for chloramphenicol transacetylase (CAT) can be utilized (Eikmanns et al. 1991, Gene 102:93–98). As will be appreciated by one skilled in the art, other non-antibiotic methods to select for maintenance of the plasmid may also be used, such as, for example a variety of auxotrophic markers (see Sambrook et al., 1989, supra; Ausubel et al., supra).

5.2.1.3 the Homology Arms

A required component of the vector is two short regions of double-stranded DNA, referred to herein as 'homology arms'. In one embodiment, as shown in FIG. 1, the two homology arms (labeled "A" and "B") are homologous to the sequence of the DNA flanking the target DNA of interest (labeled A' and B'), one arm being homologous to a DNA sequence upstream from the target DNA and the second arm being homologous to a sequence located downstream from the target DNA. As used herein, two double-stranded DNA molecules are "homologous" if they share a common region of identity, optionally interrupted by one or more base-pair differences, and are capable of functioning as substrates for homologous recombination. In a preferred embodiment, the homology arms contain approximately 22 to 100 base pairs or more of continuous identity to a double-stranded region flanking target DNA of interest. Regions of homology can be interrupted by one or more non-identical residues, provided that the homology arms are still efficient substrates for homologous recombination. In a preferred embodiment, for optimum recombination efficiency, homology arms are approximately 50 nucleotides in length, with in the range of 20–30 (e.g., 25) base pairs of continuous, uninterrupted, sequence identity. Although shorter regions of continuous identity are also possible (e.g., at least 6, 8, or 10 base pairs), lower efficiencies of recombination can be expected using such shorter regions of continuous identity. For example, in one embodiment, the length of continuous identity may be as short as 6 bp (Keim and Lark, 1990, J. Structural Biology 104: 97–106). There is no upper limit to length of homology arms or the length of their continuous identity to the flanking target DNA sequence.

Nucleotide sequences flanking a target DNA also are referred to herein as the "termini" of the target DNA. Thus, a target DNA will have two-termini, a first terminus and second terminus. The orientation of the two arms relative to the desired insert must be the same as is the orientation of the homologous sequence relative to the target DNA (see FIG. 1), so that recombination between the homology arms and the first and second termini of the target DNA results in the target DNA being inserted between the two homology arms.

The sequences of the two homology arms are chosen according to the experimental design. The only limitations on the choice of an homology arm is that it should not be a sequence found more than once within the target DNA and should not be present elsewhere in the host cell during the homologous recombination reaction. In this case, the intended homologous recombination product can still be obtained, however amongst a background of alternative homologous recombinations events. In one embodiment, the sequence of the homology arms are two sequences flanking the polylinker of a commonly used cloning vehicle such as a BAC, PAC, YAC (yeast artificial chromosome), phage cloning vectors such as the λEMBL or λGT series, phagemid, cosmid, pBR322, pGEM, pGEX, pET, baculovirus vectors, viral vectors such as adenoviral vectors and adeno-associated viral vectors. Thus, a single vector can be used to subclone any insert that has been cloned in these vectors. Vectors containing such homology arms are particularly useful for subcloning inserts derived from positive clones from a DNA library, such as a BAC, PAC, YAC, cosmid or lambda library.

In various embodiments, as described hereinbelow, the homology arms are positioned at the ends of a linear DNA molecule, or within a linear DNA molecule or circular DNA plasmid vector.

Homology arms are oriented in the same orientation relative to their orientation in the target nucleotide sequence. In other words, they are oriented so the desired DNA sequence is inserted between the arms after the recombination takes place. Where the homology arms are positioned at the ends of the linear DNA the inserted DNA sequence is captured and inserted between the two arms, thereby creating a circular and replicable plasmid.

5.2.1.4 Adapter Oligonucleotide Homology Arms

In an alternative embodiment, the nucleotide sequence of the homology arms is homologous to nucleotide sequences present on adaptor oligonucleotides. Each of two adaptor oligonucleotides comprise a nucleotide sequence homologous to nucleotide sequences present on one of the homology arms, and a second region of homology that is homologous to one of the two termini of the target DNA. Adaptor oligonucleotides are depicted in FIG. 1. The homology arms of the vector are labeled "A" and "B", and regions of the adaptor oligonucleotide homologous to these sequences are labeled A' and B'. The two termini of target DNA are labeled "C" and "D", and the corresponding homologous sequences present on the adaptor oligonucleotides are labeled C' and D'. In this embodiment, recombination mediated by RecE/T or Redα/β between the vector homology arms, the region of homology on the adaptor oligonucleotides, and the flanking termini of the target gene results in the target DNA being inserted or 'captured' between the homology arms of the vector.

5.2.1.5 Construction of the Vector

The linear fragment or circular vector may be constructed using standard methods known in the art (see Sambrook et al., 1989, supra; Ausubel et al., supra). For example, synthetic or recombinant DNA technology may be used. In one embodiment, the linear fragment is made by PCR amplification. In this method, oligonucleotides are synthesized to include the homology arm sequences at their 5' ends, and PCR primer sequences at their 3' ends. These oligonucleotides are then used as primers in a PCR amplification reaction to amplify a DNA region including an origin of replication and a selectable genetic marker. In another embodiment, a plasmid may be constructed to comprise two appropriately oriented homology arms flanking an origin of replication and a selectable genetic marker by standard recombinant DNA techniques (see e.g., Methods in Enzymology, 1987, Volume 154, Academic Press; Sambrook et al., 1989, Molecular Cloning—A Laboratory Manual, 2nd Edition, Cold Spring Harbor Press, New York; and Ausubel et al., Current Protocols in Molecular Biology, Greene Publishing Associates and Wiley Interscience, New York). The plasmid is then linearized, for example, by restriction endonuclease digestion.

In another embodiment, for example, the following method may be used to construct the vector DNA used in Section 5.1.3, above. Two oligonucleotides are synthesized, one of which includes, from 5' to 3' end, a restriction site unique to the vector, a left homology arm and a PCR primer. The other oligonucleotide includes, from 5' to 3' end, the same restriction site unique to the vector, an SSRT, a right homology arm and a PCR primer. The two homology arms are chosen to flank the target DNA. The SSRT is a site recognized by any site specific recombinase (SSR) such as Cre, Flp, Kw, or R recombinases. The synthesis of the oligonucleotide must be designed so that the two SSRTs are orientated as directed repeats in the vector. Two PCR primers are used amplify a DNA template that includes a plasmid origin, a selectable gene and an identical SSRT between the origin and the selectable gene. The product of the PCR reaction is then cut with the restriction enzyme that recognizes the sites included at the 5' ends of the oligonucleotides to permit efficient circularization by ligation. The circular product is then transformed into E. coli for amplification to yield large amounts of the vector.

In another embodiment, a linear fragment is constructed by taking plasmid with selectable marker, an origin and two cloning sites, and cloning in an oligonucleotide homology arm into each cloning site. Restriction enzymes are then used to cut the plasmid DNA to produce linear fragment bounded by the homology arms. This method is preferred for construction of more complex plasmids—e.g. plasmids containing eukaryotic enhancer and promoter elements in order to include eukaryotic expression elements. Additionally, other sequence elements may be subcloned into the vector.

The vector may also contain additional nucleotide sequences of interest for protein expression, manipulation or maintenance of the inserted target DNA. For example, promoter sequences, enhancer sequences, translation sequences such as Shine and Dalgarno sequences, transcription factor recognition sites, Kozak consensus sequences, and termination signals may be included, in the appropriate position in the vector. For recombination cloning in cells other than bacterial cells, such as plant, insect, yeast or mammalian cells, other sequence elements may be necessary, such as species-specific origins of replication, transcription, processing, and translation signals. Such elements may include, but are not limited to eukaryotic origins of replication, enhancers, transcription factor recognition sites, CAT boxes, or Pribnow boxes.

In an embodiment wherein RecE/T and/or Redα/β or other bacterial recombinase is produced recombinantly from an expression plasmid in the cell, the chosen vector must be compatible with the bacterial recombinase expression plasmid described in Section 5.2.3, below. One of skill in the art would readily be aware of the compatibility requirements necessary for expressing multiple plasmids in a single cell. Methods for propagation of two or more constructs in procaryotic cells are well known to those of skill in the art. For example, cells containing multiple replicons can routinely be selected for and maintained by utilizing vectors comprising appropriately compatible origins of replication and independent selection systems (see Miller et al., 1992, supra; Sambrook et al., 1989, supra).

5.2.2 Bacterial Recombinases

The invention described herein is described mainly with reference to the use of RecE/T and/or Redα/β. However, as will be clear to the skilled artisan, the invention is equally applicable to the use of other bacterial recombinases that have the ability to mediate homologous recombination using a pair of homologous double-stranded DNA molecules as substrates. As used herein, a bacterial recombinase is a recombinase that is expressed endogenously in bacteria, whether of phage or bacterial origin, and is capable of mediating homologous recombination. In various embodiments, the bacterial recombinase is RecE/T and/or Redα/β recombinase. In another specific embodiment, a functionally equivalent system for initiating homologous recombination comprises erf protein from phage P22. Further, individual protein components of bacterial recombinases can be substituted by other functional components for use in the present invention.

"RecE" and "RecT" as used herein, refers first, to E. coli, e.g., E. coli K12, RecE or RecT. The E. coli RecE and RecT nucleotide and amino acid sequences are well known (RecE, GenBank Accession No. M24905 and SWISS-PROT Accession No. Pl5033; RecT, GenBank Accession No. L23927 and SWISS-PROT Accession No. P33228). "Redα" and "Redβ" refer to the phage lambda encoded proteins. Redβ has a 5' to 3' exonuclease activity similar to the 5' to 3' exonuclease of RecE, and Red/β has a DNA annealing activity similar to that of RecT. Nucleotide and amino acid sequences are well known for both of these lambda proteins (see GenBank Accession Nos. J02459; M17233).

As will be clear to the skilled artisan, reference to RecE/T and/or Redα/β herein shall also apply to a combination of RecE/T and Redα/β, unless indicated otherwise explicitly or by context. In a specific embodiment, combination of the two enzyme complexes has a synergistic effect on the efficiency of recombination.

Bacterial recombinases that can be used also include allelic variants of the components of the recombinases. For example, amino acid sequences utilized in the RecE/T and Redαct recombination systems of the invention can also comprise amino acid sequences encoded by any allelic variants of RecE, RecT, Redα, or Red/β, as long as such allelic variants are functional variants, at least to the extent that they exhibit homologous recombination activity. Allelic variants can routinely be identified and obtained using standard recombinant DNA techniques (see e.g., Methods in Enzymology, 1987, volume 154, Academic Press; Sambrook et al., 1989, Molecular Cloning—A Laboratory Manual, 2nd Edition, Cold Spring Harbor Press, New York; and Ausubel et al., Current Protocols in Molecular Biology, Greene Publishing Associates and Wiley Interscience, New York), or protein evolution approaches (Kuchner et al., 1998, Curr. Opin. Biotechnol. 9:534–548).

In general, nucleic acid encoding such allelic variants should be able to hybridize to the complement of the coding sequence of RecE, RecT, Redα, or Redβ under moderately stringent conditions (using, e.g., standard Southern blotting hybridization conditions, with the final wash in 0.2×SSC/0.1% SDS at 42° C.; Ausubel et al., eds., 1989, Current Protocols in Molecular Biology, Vol. I, Green Publishing Associates, Inc., and John Wiley & sons, Inc., New York, at p. 2.10.3), or highly stringent hybridization conditions (using, e.g., standard Southern blotting hybridization conditions with the final wash in 0.1×SSC/0.1% SDS at 68° C.; Ausubel et al., supra).

RecE, RecT, Redα, and Redβ, as used herein also includes RecE, RecT, w Redα, and Redβ homologs derived from the phages hosted by, or the cells of, procaryotic cells of the family Enterobacteriaceae. Members of the family Enterobacteriaceae include, but are not limited to species of Escherichia, Salmonella, Citrobacter, Klebsiellae, and Proteus. Such RecE, RecT, Redα, or Redβ homolog is, generally, encoded by a gene present in a phage genome whose product participates in a recombination-mediated step in the phage life cycle, such as Redα and Redβ in the life cycle of lambda phage.

RecE/T homologs can routinely be identified and obtained using standard procaryotic genetic and recombinant DNA techniques (see e.g., Sambrook et al., supra., and Ausubel et al., supra). Recombinant DNA may be obtained from a cloned genomic or cDNA library, or by PCR amplification. For example, a genomic library may be produced by standard molecular biological techniques, or obtained from commercial or non-commercial sources. The genomic or cDNA library may then be screened by nucleic acid hybridization to a labeled E. coli recE or recT probe (Grunstein & Hogness, 1975, Proc.

Natl. Acad. Sci. U.S.A. 72:3961) and positive clones can be isolated and sequenced.

In a specific example, a RecE or RecT homolog can routinely be identified in Salmonella typhimurium. The recE and recT genes are well characterized in E. coli K-12; the nucleotide and protein sequences of both RecE (GenBank Accession No. M24905 and SWISS-PROT Accession No. P15033) and RecT (GenBank Accession No. L23927 and SWISS-PROT Accession No. P33228) are known; (see also Bachmann, 1990, Microbiol. Rev. 54:130–197; Rudd, 1992, in Miller, 1992, supra, pp. 2.3–2.43). A complete S. typhimurium genomic cosmid or λ library may be used. The S. typhimurium library may then be screened by hybridization with an E. coli RecE or RecT probe utilizing hybridization conditions such as those described above. For example, since the two genes are expected to be highly homologous, standard moderately stringent hybridization conditions are preferred.

In one embodiment, such conditions can include the following: Filters containing DNA can be pretreated for 6 hours at 55° C. in a solution containing 6×SSC, 5× Denhart's solution, 0.5% SDS and 100 μg/ml denatured salmon sperm DNA. Hybridizations can be carried out in the same solution and 5–22×10$^6$ cpm $^{32}$P-labeled probe is used. Filters can be incubated in hybridization mixture for 18–20 hours at 55° C., and then washed twice for 30 minutes at 60° C. in a solution containing 1×SSC and 0.1% SDS. Filters are then blotted dry and exposed to X-ray film for autoradiography. Other conditions of moderate stringency which may be used are well-known in the art. Washing of filters is done at 37° C. for 1 hour in a solution containing 2×SSC, 0.1% SDS. Subsequent isolation, purification and characterization of clones containing the S. typhimurium can be performed by procedures well known in the art (see Ausubel et al., supra). Such sequences can be used to construct the S. typhimurium RecE/Ts of the invention.

Alternatively, the S. typhimurium gene can be isolated from S. typhimurium mRNA. mRNA can be isolated from cells which express the RecE or RecT protein. A cDNA library may be produced by reverse transcription of mRNA, and screened by methods known in the art, such as those described above for screening a genomic library (see Ausubel et aL, supra). Alternatively, recE or recT cDNA can be identified by PCR techniques, such as RACE (Rapid Amplification of cDNA Ends; Ausubel et al., supra), using two primers designed from the E. coli recE or recT sequence: a "forward" primer having the same sequence as the 5' end of the E. coli recE or recT mRNA, and a "reverse" primer complementary to its 3' end. The PCR product can be verified by sequencing, subcloned, and used to construct the RecE/T of the invention. Such cDNA sequences can also be used to isolate S. typhimurium genomic recE or recT sequences, using methods well known in the art (Sambrook et al., 1989, supra; Ausubel et al., supra).

Nucleic acid molecules encoding the RecE/T recombination enzymes of the invention can, further, be synthesized and/or constructed according to recombinant and synthetic means well known to those of skill in the art (See e.g., Sambrook, supra and Ausubel et aL, supra.).

As discussed below, the ability to control the expression of the sequences such that expression can be regulatable (e.g. inducible) and such that a wide range of expression levels can be achieved is beneficial to the performance of the methods of the invention.

The nucleic acid molecules can, for example, be maintained extrachromosomally, e.g., on a plasmid, cosmid or a bacteriophage. Alternatively, the nucleic acid molecules can be integrated into the chromosome, e.g., E. coli chromosome, utilizing, for example, phage transduction or transposition. Thus, the RecE/T coding sequences can be engineered by standard techniques to be present in high copy, low copy or single copy within each cell. A variety of different regulatory sequences can be also utilized for driving expression of the recombination proteins. Each of these aspects of expression/strain construction can be manipulated to yield cells exhibiting a wide range of recombination protein expression levels. It is to be noted that single copy chromosomal versions of the recombination protein coding sequences are additionally advantageous in that such a configuration facilitates construction of strains.

5.2.2.1 Protein Expression

The bacterial recombinase may be expressed either constitutively or inducibly in bacterial, yeast, insect, or mammalian cells. In a preferred embodiment, recombination proteins are expressed in a bacterial, most preferably, *E. coli* strain. For example, the host cell may comprise the recE and recT genes located on the host cell chromosome. Examples of *E. coli* strains in which the expression of RecE/T is endogenous are known, for example, *E. coli* sbcA strains (Zhang et al., 1998, supra). Alternatively RecE/T may be recombinantly expressed from non-chromosomal DNA, preferably on a plasmid vector, e.g., pBADETγ (Zhang et al., 1998, supra) or pGETrec (Narayanan et al., 1999, Gene Therapy). Similarly Redα/β can be endogenous to strains that have integrated λ prophage, or expressed from plasmids, for example pBADαβγ (Muyrers et aL, 1999, supra). RecE/T and/or Redα/β expression constructs can be constructed according to standard recombinant DNA techniques (see e.g., Methods in Enzymology, 1987, volume 154, Academic Press; Sambrook et al. 1989, Molecular Cloning—A Laboratory Manual, 2nd Edition, Cold Spring Harbor Press, New York; and Ausubel et aL Current Protocols in Molecular Biology, Greene Publishing Associates and Wiley Interscience, New York, each of which is incorporated herein by reference in its entirety).

In one embodiment, RecE/T and/or Redα/β is expressed in *E. coli* from a high-copy plasmid such as a plasmid containing a ColE1-derived origin of replication, examples of which are well known in the art (see Sambrook et al., 1989, supra; see also Miller, 1992, A Short Course in Bacterial Genetics, Cold Spring Harbor Laboratory Press, NY, and references therein), such as pUC19 and its derivatives (Yanisch-Perron et al., 1985, Gene 33:103–119).

With respect to regulatory controls which allow expression (either regulated or constitutive) at a range of different expression levels, a variety of such regulatory sequences are well known to those of skill in the art. The ability to generate a wide range of expression is advantageous for utilizing the methods of the invention, as described below. Such expression can be achieved in a constitutive as well as in a regulated, or inducible, fashion.

Inducible expression yielding a wide range of expression can be obtained by utilizing a variety of inducible regulatory sequences. In one embodiment, for example, the lacI gene and its gratuitous inducer IPTG can be utilized to yield inducible, high levels of expression of RecE/T when sequences encoding such polypeptides are transcribed via the lacOP regulatory sequences.

RecE and RecT may be expressed from different promoters, or alternatively, the recE and recT genes may be expressed on a polycistronic mRNA from a single promoter. Such heterologous promoters may be inducible or constitutive. Preferably the expression is controlled by an inducible promoters. Inducible expression yielding a wide range of expression can be obtained by utilizing a variety of inducible regulatory sequences. In one embodiment, for example, the lacI gene and its gratuitous inducer IPTG can be utilized to yield inducible, high levels of expression of RecE/T when sequences encoding such polypeptides are transcribed via the lacOP regulatory sequences. A variety of other inducible promoter systems are well known to those of skill in the art which can also be utilized. Levels of expression from RecE/T or Redα/β constructs can also be varied by using promoters of different strengths.

Other regulated expression systems that can be utilized include but are not limited to, the araC promoter which is inducible by arabinose (AraC), the TET system (Geissendorfer M. & Hillen W., 1990, Appl. Microbiol. Biotechnol. 33:657–663), the $p_L$ promoter of phage λ temperature and the inducible lambda repressor $CI_{857}$ (Pirrotta, 1975, Nature 254: 114–117; Petrenko et al., 1989, Gene 78:85–91), the trp promoter and trp repressor system (Bennett et al, 1976, Proc. Natl. Acad. Sci USA 73:2351–55; Wame et al., 1986, Gene 46:103–112), the lacUV5 promoter (Gilbert & Maxam, 1973, Proc. Natl. Acad. Sci. USA 70:1559–63), lpp (Nokamura et al., et al., 1982, J. Mol. Appl. Gen. 1:289–299), the T7 gene-10 promoter, phoA (alkaline phosphatase), recA (Horii et al. 1980), and the tac promoter, a trp-lac fusion promoter, which is inducible by tryptophan (Amann et al., 1983, Gene 25:167–78), for example, are all commonly used strong promoters, resulting in an accumulated level of about 1 to 10% of total cellular protein for a protein whose level is controlled by each promoter. If a stronger promoter is desired, the tac promoter is approximately tenfold stronger than lacUV5, but will result in high baseline levels of expression, and should be used only when overexpression is required. If a weaker promoter is required, other bacterial promoters are well known in the art, for example, maltose, galactose, or other desirable promoter (sequences of such promoters are available from Genbank (Burks et al. 1991, Nucl. Acids Res. 19:2227–2230).

Cells useful for the methods described herein are any cells containing RecE/T and/or Redα/β recombinases. Preferably, the host cell is a gram-negative bacterial cell. More preferably, the host cell is an entero-bacterial cell. Members of the family Enterobacteriaceae include, but are not limited to, species of Escherichia, Salmonella, Citrobacter, Klebsiellae, and Proteus. Most preferably the host cell is an *Escherichia coli* cell. Cells can also be derived from any organism, including, but not limited to, yeast, fly, mouse, or human cells, provided they can be engineered to express a suitable recombinase. The recombinase is preferably RecE/T recombinase derived from *E. coli*, or Redα/β recombinase derived from phage λ, or a functionally equivalent RecE/T or Redα/β recombinase system derived from Enterobacteriaceae or an Enterobacteriaceae phage, wherein such systems can mediate recombination between regions of sequence homology.

Cells expressing RecE/T and/or Redα/β proteins may be made electrocompetent in advance and stored at −70° C.

Alternatively, the methods of the invention may be carried out in any other cell type in which expression of RecE/T and/or Redα/β is possible. For example, a variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used. In specific embodiments, the RecE/T and/or Redα/β genes are expressed, or a sequence encoding a functionally active portion of RecE/T and/or Redα/β. In yet another embodiment, a fragment of RecE/T or Redα/β comprising a domain of the RecE/T and/or Redα/β proteins are expressed.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinants (genetic recombination). Expression of nucleic acid sequence encoding a RecE/T or Redα/β protein or peptide fragment may be regulated by a second nucleic acid sequence so that the RecE/T or Redα/β protein or peptide is expressed in a host transformed with the recombinant DNA molecule. For example, expression of a RecE/T or Redα/β protein may be controlled by any promoter/enhancer element known in the art. Promoters which may be used to control RecE/T or Redα/β expression include, but are not limited to, the SV40 early promoter region (Bernoist and Chambon, 1981, Nature 290:304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); plant expression vectors comprising the nopaline synthetase promoter region (Herrera-Estrella et aL, 1984, Nature 303:209–213) or the cauliflower mosaic virus 35S RNA promoter (Gardner, et al., 1981, Nucl. Acids Res. 9:2871), and the promoter of the photosynthetic enzyme ribulose biphosphate carboxylase (Herrera-Estrella et al, 1984, Nature 310:115–120); promoter elements from yeast or other fungi such as the Gal 4 promoter, the ADC (alcohol dehydrogenase) promoter, PGK (phosphoglyceroyl kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adarnes et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5;1639–1648; Hammer et al., 1987, Science 235:53–58; alpha 1-antitrypsin gene control region which is active in the liver (Kelsey et al., 1987, Genes and Devel. 1:161–171), beta-globin gene control region which is active in myeloid cells (Mograrn et al., 1985, Nature 315:338–340; Kollias et al., 1986, Cell 46:89–94; myelin basic protein gene control region which is active in oligodendrocyte cells in the brain (Readhead et al., 1987, Cell 48:703–712); myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

In a specific embodiment, a vector is used that comprises a promoter operably linked to a bacterial recombinase (e.g., RecE or RecT)-encoding nucleic acid, one or more origins of replication, and, optionally, one or more selectable markers (e.g., an antibiotic resistance gene).

The chosen vector must be compatible with the vector plasmid described in Section 5.2.1, above. One of skill in the art would readily be aware of the compatibility requirements necessary for maintaining multiple plasmids in a single cell. Methods for propagation of two or more constructs in procaryotic cells are well known to those of skill in the art. For example, cells containing multiple replicons can routinely be selected for and maintained by utilizing vectors comprising appropriately compatible origins of replication and independent selection systems (see Miller et al., 1992, supra; Sambrook et al., 1989, supra).

5.2.3 Host Cells

The host cell used for the cloning methods of the present invention and for propagation of the cloned DNA can be any cell which expresses the recE and recT and/or redα and redβ gene products, or any cell in which heterologous expression of these genes is possible. Examples of possible cell types that can be used include, but are not limited to, prokaryotic eukaryotic cells such as bacterial, yeast, plant, rodent, mice, human, insect, or mammalian cells. In a preferred embodiment, the host cell is a bacterial cell. In the most preferred embodiment, the host cell is an *E. coli* cell. Examples of specific *E. coli* strains that can be used are JC 8679 and JC 9604. The genotype of JC 8679 and JC 9604 is Sex (Hfr, F+, F−, or F'): F−.JC 8679 comprises the mutations: recBC 21, recC 22, sbcA 23, thr-1, ara-14, leu B 6, DE (gpt-proA) 62, lacY1, tsx-33, gluV44 (AS), galK2 (Oc), LAM-his-60, relA 1, rps L31 (strR), xyl A5, mtl-1, argE3 (Oc) and thi-1. JC 9604 comprises the same mutations and further the mutation recA 56.

In an alternative embodiment, a eukaryotic cell may be used as a host cell for the cloning and subcloning methods described herein. Any cell that expresses or can be engineered to express a bacterial recombinase, or functional equivalents thereof, can be used. Cell lines derived from human, mouse, monkey, or any other organism may be used. For example, non-limiting examples of cell lines useful for the methods of the invention include CHO, VERO, BHK, HeLa, COS, Md.CK, 293, 3T3, and WI38 cells.

A variety of host-vector systems may be utilized to introduce and express the protein-coding sequence of RecE/T, Redα/β or a functionally equivalent system. Such methods are well known in the art (see Ausubel et aL, Current Protocols in Molecular Biology, Greene Publishing Associates and Wiley Interscience, New York). These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA. Methods for protein expression are also discussed in Section 5.2.2, above.

5.2.4 Target DNA

The target DNA is chosen according to experimental design, and may be any double-stranded DNA as short as one base pair or over one hundred kilobases in length. In a specific embodiment, the target is up to 100, 125, 200, or 300 kb in length. In another specific embodiment, the target DNA is 25 to 100 kilobases, e.g., as present in a BAC vector. Other specific embodiments of target DNAs are set forth in the Examples in Section 6. The target DNA may reside on any independently replicating DNA molecule such as, but not limited to, a plasmid, BAC or the *E. coli* chromosome. The target DNA may also reside on any source of DNA including, but not limited to, DNA from any prokaryotic, archaebacterial or eukaryotic cell, or from viral, phage or synthetic origins. For example, nucleic acid sequences may be obtained from the following sources: human, porcine, bovine, feline, avian, equine, canine, insect (e.g., Drosophila), invertebrate (e.g. C. elegans), plant, etc. The DNA may be obtained by standard procedures known in the art (see, e.g., Sambrook et al., 1989, Molecular Cloning, A Laboratory Manual, 2d Ed., Cold Spring Harbor Laboratory Press, Cold Spring Harbor, N.Y.; Glover (ed.), 1985, DNA Cloning: A Practical Approach, MRL Press, Ltd., Oxford, U.K. Vol. I, II).

5.3 Methods for use of the Invention
5.3.1 Introduction of DNA into Host Cells Any method known in the art for delivering a DNA preparation comprising the target DNA into a host cell is suitable for use with the methods described above. Such methods are known in the art and include, but are not limited to electroporation of cells, preparing competent cells with calcium or rubidium chloride, transduction of DNA with target DNA packaged in viral particles. For eukaryotic cells, methods include but are not limited to electroporation, transfection with calcium phosphate precipitation of DNA, and viral packaging. In a preferred embodiment, electroporation is used. Cells containing RecE/T or Redα/β proteins are treated to make them competent for electroporation by standard methods (see Ausubel et al., Current Protocols in Molecular Biology, Greene Publishing Associates and Wiley Interscience, New York). Preferably, about 50 μl of a standard preparation of electro-competent cells is used for electroporation by standard procedures. In experiments that require the transformation of a linear or circular vector, 0.3 μg or more of vector is preferably used. In experiments that require the transformation of a DNA preparation containing the target DNA, 0.3 μg or more is preferably used. For co-transformation experiments, the DNAs are preferably mixed before electroporation. After electroporation, the cells are preferably diluted in culture medium and incubated for an approximately 1 and a half hours recovery period before culturing under conditions to identify the phenotypic change conveyed by the selectable marker gene.

In experiments utilizing site-specific recombination or endonuclease cleavage of the vector, expression of the SSR or the endonuclease, or combinations of an SSR and an endonuclease or two SSRs, is induced either before preparation of electrocompetent cells, during the recovery period after electroporation, or during culture to identify the selectable marker.

Optimally the phenotypic change is resistance to an antibiotic and the cells are cultured on plates that contain the corresponding antibiotic. In this case, the antibiotic resistant colonies that appear after overnight culture will predominantly contain the desired subcloning product.

In another embodiment, DNA is delivered into the host cell by transduction of DNA that has been packaged into a phage particle. P1 or λ transduction and packaging protocols are known in the art. λ packaging extracts are available commercially (e.g., from Promega, Madison, Wis.).

5.3.2 Oligonucleotides

The oligonucleotide homology arms, primers, and adapter oligonucleotides used in conjunction with the methods of the invention are often oligonucleotides ranging from 10 to about 100 nucleotides in length. In specific aspects, an oligonucleotide is 10 nucleotides, 15 nucleotides, 20 nucleotides, 50 nucleotides, or 100 nucleotides in length, or up to 200 nucleotides in length. In the preferred embodiment, the oligonucleotide is approximately 90 nucleotides in length.

Oligonucleotides may be synthesized using any method known in the art (e.g., standard phosphoramidite chemistry on an Applied Biosystems 392/394 DNA synthesizer). Further, reagents for synthesis may be obtained from any one of many commercial suppliers.

An oligonucleotide or derivative thereof used in conjunction with the methods of this invention may be synthesized using any method known in the art, e.g., by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16, 3209), methylphosphonate oligonucleotides can be prepared by use of controlled pore glass polymer supports (Sarin et al., 1988, Proc. Nat'l Acad. Sci. U.S.A. 85, 7448–7451), etc.

An oligonucleotide may comprise at least one modified base, provided that such modification does not interfere with homologous recombination. For example, such modifications may include, but are not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, and 2,6-diaminopurine.

An oligonucleotide may comprise at least one modified phosphate backbone, provided that such modification does not interfere with homologous recombination. Such modification may include, but is not limited to, a phosphorothioate, a phosphorodithioate, a phosphoramidothioate, a phosphoramidate, a phosphordiamidate, a methylphosphonate, an alkyl phosphotriester, and a formacetal or analog thereof.

5.3.3 DNA Amplification

The polymerase chain reaction (PCR) is optionally used in connection with the invention to amplify a desired sequence from a source (e.g., a tissue sample, a genomic or cDNA library). Oligonucleotide primers representing known sequences can be used as primers in PCR. PCR is typically carried out by use of a thermal cycler (e.g., from Perkin-Elmer Cetus) and a thermostable polymerase (e.g., Gene Amp™ brand of Taq polymerase). The nucleic acid template to be amplified may include but is not limited to mRNA, cDNA or genomic DNA from any species. The PCR amplification method is well known in the art (see, e.g., U.S. Pat. Nos. 4,683,202, 4,683,195 and 4,889,818; Gyllenstein et al., 1988, Proc. Nat'l. Acad. Sci. U.S.A. 85, 7652–7656; Ochman et al., 1988, Genetics 120, 621–623; Loh et al, 1989, Science 243, 217–220).

5.4 Methods for Diagnostic Applications

The methods of the present invention may be used to detect, prognose, diagnose, or monitor various infections, conditions, diseases, and disorders associated with the presence of a foreign DNA or variant DNA, or monitor the treatment thereof. For example, as described in Section 5.4.1, below, the methods may be used to detect, prognose, diagnose, or monitor various infections and diseases, such as diseases associated with a viral infection, a bacterial infection, or infection by a protozoan, parasite, or other known pathogen. As described in Section 5.4.2, below, the methods can also be used to detect, prognose, diagnose, or monitor various infections, conditions, diseases, and disorders associated with the presence of variant DNA, such as a genetic mutation or a single nucleotide polymorphism (SNP). Methods for such diagnostic purposes are described in detail hereinbelow.

5.4.1 Detection of Foreign DNA

The methods of the invention described hereinabove can be used to detect foreign DNA, such as a viral or bacterial DNA, stemming from exposure to a pathogen, in a patient exposed to the pathogen. The patient may or may not exhibit the symptoms of infection by the pathogen or the presence of a disease or disorder associated by the presence of the pathogen. In one embodiment, for example, a target DNA sample can be prepared from the DNA from a patient having or suspected of having such a disease or infection. Homology arms having sequence homology to a foreign target DNA can be designed and prepared. The sample DNA can then be introduced into an *E. coli* host cell that expresses a bacterial recombinase and that contains the vector DNA, by any of the methods described in Section 5.1, above. In an alternative embodiment, adaptor oligonucleotides can be designed comprising a first sequence homologous to a vector sequence and a second sequence homologous to the foreign target DNA, oriented as described in detail in Section 5.1, above. Such adaptor oligonucleotides can be used either to co-transfect, together with the sample DNA and the vector DNA, an *E. coli* host cell that expresses RecE/T or Redα/β, or can be transfected directly into cells that already comprise vector DNA and sample DNA. Cells are then grown in selective media, as described in Section 5.1 above, and cells that resist selection can be analyzed for the presence of an insert of the appropriate size.

The target DNA can be isolated from a patient or subject's biological sample, such as, but not limited to, whole blood, plasma, serum, skin, saliva, urine, lymph fluid, cells obtained from biopsy aspirate, tissue culture cells, media, or non-biological samples such as food, water, or other material. Methods for preparation of DNA from such sources are well known to those of skill in the art (see, e.g., Current Protocols in Molecular Biology series of laboratory technique manuals, 1987–1994 Current Protocols, 1994–1997 John Wiley and Sons, Inc.).

In one embodiment, for example, where it is desired to detect or diagnose a viral infection or disease, the homology arms can comprise DNA sequences homologous to DNA sequences of known viral DNA. The methods can be used to detect and isolate viral DNA either as a viral DNA strand, or a DNA replicative intermediate of a DNA or an RNA virus.

In one embodiment, for example, DNA genomes or replicative intermediates of DNA viruses may be directly targeted using homology arm sequences designed to be homologous to viral sequences of such DNA viruses including, but not limited to, hepatitis type B virus, parvoviruses, such as adeno-associated virus and cytomegalovirus, papovaviruses such as papilloma virus, polyoma viruses, and SV40, adenoviruses, herpes viruses such as herpes simplex type I (HSV-I), herpes simplex type II (HSV-II), and Epstein-Barr virus, and poxviruses, such as variola (smallpox) and vaccinia virus. In another embodiment, the replicative intermediates of retroviral RNA viruses that replicate through a DNA intermediate may be directly targeted using homology arm sequences designed to be homologous to viral sequences of such RNA viruses, including but not limited to human immunodeficiency virus type I (HIV-I), human immunodeficiency virus type II (HIV-II), human T-cell lymphotropic virus type I (HTLV-I), and human T-cell lymphotropic virus type II (HTLV-II). In another embodiment, in order to detect and isolate the genomic or replicative intermediates of RNA virus that replicate through an RNA intermediate, RNA may be isolated and transcribed into a cDNA copy of the RNA using reverse transcriptase according to methods well known in the art. Such cDNA copies may be used as target DNA to detect the presence of RNA viruses such as influenza virus, measles virus, rabies virus, Sendai virus, picornaviruses such as poliomyelitis virus, coxsackieviruses, rhinoviruses, reoviruses, togaviruses such as rubella virus (German measles) and Semliki forest virus, arboviruses, and hepatitis type A virus.

In another preferred embodiment, where it is desired to diagnose or detect bacterial infections, the homology arms can comprise DNA sequences homologous to DNA sequences of known bacteria. For example, in one embodiment, such homology arm DNA sequences may be homologous to cDNA or genomic DNA of a pathogenic bacteria including, but not limited to, *Streptococcus pyogenes, Streptococcus pneumoniae, Neisseria gonorrhoea, Neisseria meningitidis, Corynebacterium diphtheriae, Clostridium botulinum, Clostridium perfringens, Clostridium tetani, Haemophilus influenzae, Klebsiella pneumoniae, Klebsiella ozaenae, Klebsiella rhinoscleromotis, Staphylococcus aureus, Vibrio cholerae, Escherichia coli, Pseudomonas aeruginosa, Campylobacter (Vibrio) fetus, Campylobacter jejuni, Aeromonas hydrophila, Bacillus cereus, Edwardsiella tarda, Yersinia enterocolitica, Yersinia pestis, Yersinia pseudotuberculosis, Shigella dysenteriae, Shigella flexneri, Shigella sonnei, Salmonella typhimurium, Treponema pallidum, Treponema pertenue, Treponema carateneum, Borrelia vincentii, Borrelia burgdorferi, Leptospira icterohemorrhagiae, Mycobacterium tuberculosis, Toxoplasma gondii, Pneumocystis carinii, Francisella tularensis, Brucella abortus, Brucella suis, Brucella melitensis, Mycoplasma* spp., *Rickettsia prowazeki, Rickettsia tsutsugumushi, Chlamydia* spp., and *Helicobacter pylori.*

In another embodiment, such homology arm DNA sequences may be homologous to cDNA or genomic DNA of a pathogenic fungi including, but not limited to, *Coccidioides immitis, Aspergillus fumigatus, Candida albicans, Blastomyces dermatitidis, Cryptococcus neoformans,* and *Histoplasma capsulatum.*

In another preferred embodiment, where it is desired to diagnose or detect protozoal infections, the homology arms can comprise DNA sequences homologous to DNA sequences of known protozoan. For example, such homology arm DNA sequences may be homologous to cDNA or genomic DNA of any known protozoan. Especially interesting are pathogenic protozoans such as *Entomoeba histolytica, Trichomonas tenas, Trichomonas hominis, Trichomonas vaginalis, Trypanosoma gambiense, Trypanosoma rhodesiense, Trypanosoma cruzi, Leishmania donovani, Leishmania tropica, Leishmania braziliensis, Pneumocystis pneumonia, Plasmodium vivax, Plasmodium falciparum,* and *Plasmodium malaria.*

In yet another preferred embodiment, where it is desired to diagnose or detect parasitic infections, the homology arms can comprise DNA sequences homologous to DNA sequences of known parasite. For example, such homology arm DNA sequences may be homologous to cDNA or genomic DNA of any known parasite including, such as Hehninths including, *Enterobius vermicularis, Trichuris trichiura, Ascaris lumbricoides, Trichinella spiralis,*

*Strongyloides stercoralis, Schistosoma japonicum, Schistosoma mansoni, Schistosoma haematobium,* and hookworms.

5.4.2 Diagnosis of Mutations and Polymorphisms in Cellular DNA

The methods of the invention can also be used to isolate and detect genetic disorders in a patient's sample, and to prognose, diagnose, or monitor various conditions, diseases, and disorders associated with the presence of variant DNA, such as a genetic mutation or a single nucleotide polymorphism (SNP), as well as to detect a genetic disposition for developing a disease or disorder.

In one embodiment, for example, a target DNA sample can be prepared from DNA isolated from a sample from a patient having or suspected of having such a genetic disease or disorder. In a preferred embodiment, a vector comprising homology arms having sequence homologous to a particular gene of interest or genomic region of interest can be designed and prepared, and, introduced into an *E. coli* host cell that expresses a bacterial recombinase such as RecE/T and/or Redα/β. The sample DNA can then be introduced into the host cell. In an alternative embodiment, adaptor oligonucleotides can be designed comprising a first sequence homologous to a vector sequence and a second sequence homologous to the DNA of the target gene of interest, oriented as described in detail in Section 5.1, above. In a preferred embodiment, such adaptor oligonucleotides can be used either to co-transfect, together with the sample DNA, an *E. coli* host cell that expresses RecE/T and/or Redα/β and contains the vector DNA. Alternatively, any of the other methods for homologous recombination cloning described in detail in Section 5.1, above, can be used. Cells are then grown in selective media, as described in Section 5.1 above, and cells that resist selection can be analyzed for the presence of an insert of the appropriate size. DNA can then be analyzed for the presence of a mutation or DNA variation of interest by restriction analysis or sequencing techniques well known in the art (see, e.g., Current Protocols in Molecular Biology series of laboratory technique manuals, 1987–1994 Current Protocols, 1994–1997 John Wiley and Sons, Inc.).

In an alternative embodiment, the homology arm or adaptor oligonucleotide may contain the sequence of the genetic mutation or DNA polymorphism of interest. In this embodiment, recombination will only occur if the sample DNA contains the mutation. This may be useful for diagnostic screening of a large number of samples for a particular mutation or DNA polymorphism, since only cells containing a particular mutation will be resistant to selection.

The target DNA may be obtained from any DNA sample, such as genomic DNA, cDNA, or mitochondrial DNA. In one embodiment, for example, the target DNA can be a region of a human chromosome. In another embodiment, the target DNA is present in a mixed population, e.g., a population of genomic DNAs derived from a plurality of subjects of interest, for example, subjects afflicted with a particular disorder. Such target DNA can be obtained from a biological sample, such as, but not limited to, whole blood, plasma, serum, skin, saliva, urine, lymph fluid, cells obtained from biopsy aspirate, tissue culture cells, media, or non-biological samples such as food, water, or other material. Methods for preparation of DNA from such sources are well known to those of skill in the art (see, e.g., Current Protocols in Molecular Biology series of laboratory technique manuals, 1987–1994 Current Protocols, 1994–1997 John Wiley and Sons, Inc.).

Non-limiting examples of genetic disorders that can be tested using this method include mutations and SNPs associated with such hereditary diseases as Brca-1 associated with breast cancer, mutations implicated in cystic fibrosis, Tay-Sachs disease, sickle cell anemia, hemophilia, atherosclerosis, diabetes, leukemia, prostrate and other cancers, and obesity. Such hereditary diseases may include degenerative and non-degenerative neurological diseases such as Alzheimer's disease, Parkinson's disease, amyotrophic lateral sclerosis, Huntington's disease, Wilson's disease, spinal cerebellar ataxia, Friedreich's ataxia and other ataxias, prion diseases including Creutzfeldt-Jakob disease, dentatorubral pallidoluysian atrophy, spongiform encephalopathies, myotonic dystrophy, depression, schizophrenia, and epilepsy. Hereditary diseases may also include metabolic diseases such as, for example, hypoglycemia or phenylketonuria. Cardiovascular diseases and conditions are also included, non-limiting examples of which include atherosclerosis, myocardial infarction, and high blood pressure. The invention can further be used for detection and diagnosis of Lyme disease, tuberculosis, and sexually transmitted diseases.

In another embodiment, the homologous recombination cloning methods of the invention can be used for determining the genetic basis of a disease or disorder. For example, target DNA can be isolated from a sample of a patient or patients afflicted with a disorder whose genetic basis is not known. In one embodiment, the cloning methods could be used to isolate a region of a chromosome known or suspected to be implicated in such a disease or disorder, from a group of patients known or suspected of having such a disorder. The recovered DNA can then be isolated and analyzed further for the presence of genetic mutations or polymorphisms, using techniques well known in the art for mapping variations in DNA, such as restriction fragment length polymorphism, or other SNP detection techniques (see, e.g., Nikiforov et al., U.S. Pat. No. 5,679,524 issued Oct. 21, 1997; McIntosh et al., PCT publication WO 98/59066 dated Dec. 30, 1998; Goelet et al., PCT publication WO 95/12607 dated May 11, 1995; Wang et al., 1998, Science 280:1077–1082; Tyagi et al, 1998, Nature Biotechnol. 16:49–53; Chen et al., 1998, Genome Res. 8:549–556; Pastinen et al., 1996, Clin. Chem. 42:1391–1397; Chen et al., 1997, Proc. Natl. Acad. Sci. 94:10756–10761; Shuber et al., 1997, Hum. Mol. Gen. 6:337–347; Liu et al., 1997, Genome Res. 7:389–398; Livak et al., 1995, Nature Genet. 9:341–342; Day and Humphries, 1994, Annal. Biochem. 222:389–395).

Non-limiting examples of target disorders of clinical interest include asthma, arthritis, psoriasis, excema, allergies, drug resistance, drug toxicity, and cancers such as, but not limited to, human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenström's macroglobulinemia, and heavy chain disease. The homologous recombination cloning methods can further be useful in diagnosing and detecting genetic differences and diagnosis of patients with autoimmune diseases, including but not limited to, insulin dependent diabetes mellitus, multiple sclerosis, systemic lupus erythematosus, Sjogren's syndrome, scleroderma, polymyositis, chronic active hepatitis, mixed connective tissue disease, primary biliary cirrhosis, pernicious anemia, autoimmune thyroiditis, idiopathic Addison's disease, vitiligo, gluten-sensitive enteropathy, Graves' disease, myasthenia gravis, autoimmune neutropenia, idiopathic thrombocytopenia purpura, rheumatoid arthritis, cirrhosis, pemphigus vulgaris, autoimmune infertility, Goodpasture's disease, bullous pemphigoid, discoid lupus, ulcerative colitis, and dense deposit disease.

Homologous recombination cloning methods may also be used for isolating, diagnosing, and detecting DNA mutations, alterations, variations, and SNPs not associated with disease. Non-limiting examples include such DNA mutations, alterations, variations, and SNPs present in non-coding genomic sequences, or DNA mutations, alterations, variations, and SNPs associated with different human blood groups.

In a preferred aspect of the invention, the methods of the invention may have particular utility in the isolation, detection, diagnosis, prognosis, or monitoring of human DNA mutations, alterations, variations, and SNPs. It is appreciated, however, that the methods described herein will be useful in isolating, detecting, diagnosing, prognosing, or monitoring diseases of other mammals, for example, farm animals including cattle, horses, sheep, goat, and pigs, household pets including cats and dogs; and plants including agriculturally important plants and garden plants.

5.5 Kits

The invention further provides kits that facilitate the use of the homologous recombination cloning and subcloning methods described herein. In one embodiment, a kit is provided comprising, in one or more containers: A) a double-stranded DNA vector useful for directed cloning and subcloning of a target DNA molecule of interest, said vector comprising an origin of replication and two homology arms, in the following order from 5' to 3' along a vector DNA strand: a first homology arm, the origin of replication and a second homology arm; such that the nucleotide sequence of the first homology arm on a first vector DNA strand is homologous to the sequence of the first terminus on a first target DNA strand, and the nucleotide sequence of the second homology arm on the first vector DNA strand is homologous to the nucleotide sequence of the second terminus on the first target DNA strand; and b) a cell containing a bacterial recombinase. The cell can endogenously or recombinantly express the recombinase.

In another embodiment, a kit useful for directed cloning or subcloning of a target DNA molecule in one or more containers is provided, comprising: a) a double-stranded DNA vector useful for directed cloning and subcloning of a target DNA molecule of interest, said vector comprising an origin of replication and two homology arms, in the following order from 5' to 3' along a vector DNA strand: a first homology arm, the origin of replication and a second homology arm; such that the nucleotide sequence of the first homology arm on a first vector DNA strand is homologous to the sequence of the first terminus on a first target DNA strand, and the nucleotide sequence of the second homology arm on the first vector DNA strand is homologous to the nucleotide sequence of the second terminus on the first target DNA strand; and b) a first double-stranded oligonucleotide comprising a first oligonucleotide DNA strand comprising, in the following order, from 3' to 5': a first sequence and a second sequence, said first nucleotide sequence being homologous to the nucleotide sequence of the first homology arm on said vector DNA strand, and said second nucleotide sequence being homologous to the nucleotide sequence of a first terminus on a target DNA strand; c) a second oligonucleotide comprising a second oligonucleotide strand comprising, in the following order, from 3' to 5': a third nucleotide sequence and a fourth nucleotide sequence, said third nucleotide sequence being homologous to the nucleotide sequence of the second homology aim on said vector DNA strand and said fourth nucleotide sequence being homologous to the nucleotide sequence of a second terminus on said target DNA strand; and d) a cell containing bacterial recombinase proteins, e.g., RecE/T and/or Redα/β proteins. In a specific embodiment, the cell is an *E. coli* cell.

In another embodiment, a kit is provided with one or more containers comprising: a) a double-stranded DNA vector useful for directed cloning and subcloning of a target DNA molecule of interest, said vector comprising an origin of replication and two homology arms, in the following order from 5' to 3' along a vector DNA strand: a first homology arm, the origin of replication and a second homology arm; such that the nucleotide sequence of the first homology arm on a first vector DNA strand is homologous to the sequence of the first terminus on a first target DNA strand, and the nucleotide sequence of the second homology arm on the first vector DNA strand is homologous to the nucleotide sequence of the second terminus on the first target DNA strand; b) a first double-stranded oligonucleotide comprising a first oligonucleotide DNA strand comprising, in the following order, from 3' to 5': a first nucleotide sequence and a second nucleotide sequence, said first nucleotide sequence being homologous to the nucleotide sequence of the first homology arm on said vector DNA strand, and said second nucleotide sequence being homologous to the nucleotide sequence of a first terminus on a target DNA strand; and c) a second oligonucleotide comprising a second oligonucleotide strand comprising, in the following order, from 3' to 5': a third nucleotide sequence and a fourth nucleotide sequence, said third nucleotide sequence being homologous to the nucleotide sequence of the second homology arm on said vector DNA strand and said fourth sequence being homologous to the nucleotide sequence of a second terminus on said target DNA strand.

In various specific embodiments, the target DNA of the kit is bacterial, viral, parasite, protozoan, or pathogenic DNA. In other specific embodiments, the kit's target DNA can comprise a genetic mutation or polymorphism known or suspected to be associated with a disorder or disease. In another specific embodiment, in oligonucleotide adaptor sequences or vector homology arms have sequence homology to BAC, PAC, lambda, plasmid or YAC based cloning vectors.

6. EXAMPLE

RECE/T and Redα/β Subcloning

The Examples presented in this section describe a number of experiments which demonstrate the successful cloning using the homologous recombination methods of the invention. Different approaches to subcloning methods are shown. Of particular note, one example shows the successful cloning of an insert larger than any described previously—the directed subcloning of a 25 kB DNA fragment from an approximately 150 kb BAC vector.

6.1 Methods and Materials
Preparation of Linear Fragments

Standard PCR reaction conditions were used to amplify linear DNA fragments. The 1972 bp of p15A origin plus kanamycin-resistance gene (from Tn903) from pACYC177 was amplified. The origin p15A allows this plasmid or recombinant to co-exist in cells with other plasmids that carry a ColE1 compatibility group origin. The 1934 bp of chloramphenicol (from Tn9) resistant gene plus p15A origin was amplified from pACYC184.

The oligonucleotides used in the PCR reaction comprised, at their 3' ends, and 18–30 nucleotide sequence to serve as a primer on pACYC plasmids, and at the 5' ends, a 50 to 60 nucleotide stretch of sequence homologous to the flanks of the target DNA region. For long oligonucleotides, the PCR reaction annealing temperature used was 62° C. PCR products were purified by using QIAGEN PCR Purification Kit (QIAGEN) and eluted with dH$_2$O. The template DNA was eliminated by digesting PCR products with Dpn I. After digestion, PCR products were precipitated by ethanol and resuspended in dH$_2$O at 0.5 μg/ul.

Preparation of Competent Cells

Electroporation competent cells were prepared by standard methods. Briefly, overnight cultures were diluted 100 times into LB medium with appropriate antibiotics. E. coli cells were grown to an optical density of OD$_{600}$=0.25~0.4 and were chilled on ice for 15 min. Bacterial cells were centrifuged at 7,000 rpm for 10 min at –5° C. The bacterial cell pellet was resuspended in ice-cold 10% glycerol and pelleted by centrifugation at 7,000 rpm at –5° C. for 10 min. After 3 times washing in ice-cold 10% glycerol and recentrifugation, the cell pellet was suspended in a volume of ice-cold 10% glycerol equal to volume of cells. The competent cells were divided into 50 μl aliquots in eppendorf tubes, snap frozen in liquid nitrogen and stored at –70° C.

Experiments with the plasmids pBAD-ETγ or pBAD-αβγ involved transformation of these plasmids into E. coli hosts by standard means, followed by growth overnight to saturation in LB medium plus 0.2% glucose, 50 μg/ml ampicillin, the cultures were then diluted 100 fold into LB plus 50 μg/ml ampicillin and growth to OD$_{600}$ of 0.15. L-Arabinose was then added to 0.1% of final concentration. The cells were grown to OD$_{600}$ of 0.25~0.4 before chilling on ice for 15 min.

Electroporation A solution of DNA in 1 μl (containing approximately 0.5 μg DNA or more for contransformation, or approximately 0.3 μg vector DNA or more only for cells harboring the target, or approximately 0.5 μg DNA or more containing the target for cells harboring the vector) was mixed with competent cells. The cells—DNA mixture was transferred into an ice-cold cuvette. Electroporation was performed using a Bio-Rad Gene Pulser set to 25 μFD, 2.3 kV with Pulse Controller set at 200 ohms. LB medium (1 ml) was added after electroporation. The cells were incubated at 37° C. for 1–1.5 hour with shaking and then spread on plates containing the antibiotic corresponding to the selectable marker gene in the vector.

6.2 Results

Table 1 summarizes six experiments in which various target DNA regions of interest were subcloned using different sources of RecE/T or Redα/β expression. The first column, entitled "ET expression" refers to the source of RecE/T or Redα/β, either endogenous RecE/T in E. coli hosts JC8679 or JC9604, or from plasmids pBAD-recE/T or pBADαβγ, as indicated. The second column indicates the E. coli host used. The third column indicates the target genes.

In the first experiment, the recE/T gene resident in the E. coli chromosome was subcloned in the E. coli strain JC8679, in which expression of RecE/T is constitutive. This was accomplished using the strategy outlined in FIG. 2. Oligonucleotides were designed and synthesized having the following sequence:
5'-TTCCTCTGTATTAACCGGGGAATACAGTGTAAT CGATAATTCAGAGGAATAGCTCGAGTTAATAAG ATGATCTTCTTGAGATCG-3' (SEQ ID NO: 1)
and
5'-CAGCAATGTCATCGAGCTGAGACTTACTGATA CCGGGACCCGCGTGGTAATTCTCGAGTGATTA GAAAAACTCATCGAGCATC-3' (SEQ ID NO:2)
to amplify the p15A origin of replication and Tn903 kanamycin resistant gene present in pACYC177. The results of this experiment are summarized in the first row of Table 1.

TABLE I

| ET expression | E. coli host | Target genes | Total colonies | % correct (of 18) |
| --- | --- | --- | --- | --- |
| Endogenous recE/T | JC8679 | recE/T in E. coli chromosome | 540 | 89 |
| Endogenous recE/T | JC8679 | lacZ in E. coli chromosome | 760 | 94 |
| Endogenous recE/T | JC9604 | lacZ in E. coli chromosome | 290 | 100 |
| pBAC-recE/T | JC5519 | Gentamicin in high copy plasmid | >3,000 | 100 |
| pBAD-αBγ | HB101 | lacZ in E. coli chromosome | 370 | 94 |
| pBAD-αBγ | HS996 | Intron3 of mAF4 in BAC | 160 | 83 |

In the second experiment, the lacZ gene resident in the E. coli chromosome was subcloned in the E. coli strain JC8679, in which expression of RecE/T is constitutive. This was accomplished using the strategy outlined in FIG. 2. The vector was made by PCR using oligonucleotides of the following sequence:
5'-TCAACATTAAATGTGAGCGAGTAACAACCCGT CGGATTCTCCGTGGGAACAAACGGGAATTCT GATTAGAAAAACTCATCGAGCATCAAATG-3' (SEQ ID NO:3)
and
5'-TCAGGGGAAAACCTTATTTATCAGCCGGAAAA CCTACCGGATTGATGGTAGGGATCCTTAATAAG ATGATCTTCTTGAGATCG-3' (SEQ ID NO:4)
to amplify the p15A origin of replication and Tn903 kanamycin resistance gene present in pACYC177. Results are summarized in the second row of Table 1.

In the third experiment, the lacZ gene resident in the E. coli chromosome was subcloned in the E. coli strain JC9604, in which expression of RecE/T is constitutive. This was accomplished using the strategy outlined in FIG. 2. The vector was made by PCR using oligonucleotides of the following sequence:

5'-TCAACATTAAATGTGAGCGAGTAACAACCCGT CGGATTCTCCGTGGGAACAAACGGGAATTCTG ATTAGAAAAACTCATCGAGCATCAAATG-3' (SEQ ID NO: 5)
and
5'-TCAGGGGAAAACCTTATTTATCAGCCGGAAAA CCTACCGGATTGATGGTAGGGATCCTTAATAAG ATGATCTTCTTGAGATCG-3' (SEQ ID NO:6)
to amplify the p15A origin of replication and Tn903 kanamycin resistance gene present pACYC 177. Results are summarized in the third row of Table 1.

In the fourth experiment, the gentamicin gene resident on the high copy plasmid pFastBACI (Gibco) was subcloned in the E. coli strain JC5519 using the strategy outlined in FIG. 3. Expression of RecE/T was provided by the plasmid pBAD-recE/T after this plasmid had been transformed into JC5519, followed by arabinose induction before preparation of competent cells. The vector was made by PCR using oligonucleotides of the following sequence:
5'-TGCACTTTGATATCGACCCAAGTACCGCCACCT AACAATTCGTTCAAGCCGAGGATCCTTAATAA GATCATCTTCTGAGATCGTTTTGG-3' (SEQ ID NO:7)
and
5'-TGCATTACAGTTTACGAACCGAACAGGCTTAT GTCAACTGGGTTCGTGCCTTCAGAATTCTGAT TAGAAAAACTCATCGAGCATCAAATG-3' (SEQ ID NO:8)
to amplify the p15A origin of replication and Tn903 kanamycin resistance gene present in pACYC177, the PCR product was mixed with BaamHI digested pFastBAC1 for cotransformation and plating onto gentamicin plus kanamycin containing plates.

In the fifth example, the lacZ gene resident in the E. coli chromosome was subcloned in the E. coli strain HB101 using the strategy outlined in FIG. 2. Expression of Redα/β was provided by the plasmid pBADαβγ after this plasmid had been transformed into HB101, followed by arabinose induction before preparation of competent cells. The vector was made by PCR using oligonucleotides of the following sequence:
5'-TCAACATTAAATGTGAGCGAGTAACAACCCGT CGGATTCTCCGTGGGAACAAACGGGAATTCTG ATTAGAAAAACTCATCGAGCATCAAATG-3' (SEQ ID NO:9)
and
5'-TCAGGGGAAAACCTTATTTATCAGCCGGAAAA CCTACCGGATTGATGGTAGGGATCCTTAATAAG ATGATCTTCTTGAGATCG-3' (SEQ ID NO:10)
to amplify the p15A origin of replication and Tn903 kanamnycin resistance gene present in pACYC 177. Results of this experiment are summarized in the fifth row of Table 1.

In the sixth experiment, a 25 kb region of an approximately 150 kb BAC clone carrying the mouse AF4 gene was sub cloned in the E. coli strain HS996 using the strategy outlined in FIG. 3. Expression of Redα/β was provided by the plasmid pBADαβγ after this plasmid had been transformed into HS996, followed by arabinose induction before preparation of competent cells. The vector was made by PCR using oligonucleotides of the following sequence:
5'-TGTAGCTGAGCCCAGGGGCAAGGCTGCTTTGT ACCAGCCTGCTGTCTGCGGGGGCATCACCTGG AATTCTTAATAAGATGATCTTCTTGAGATCGT TTTGG-3 ' (SEQ ID NO: 11)
and
5'-TGGGTGTCAACCTCAGGCTTTCTCACACGCAA TACAGGTAGGGACTTGCACCCCTACACACCGA ATTCTGATTAGAAAAACTCATCGAGCATCAAATG-3' (SEQ ID NO:12)
to amplify the p15A origin of replication and Tn903 kanamycin resistance gene present in pACYC177. The PCR product was mixed with 0.5 μg purified BAC DNA for cotransformation. Results of this experiment are summarized in the sixth row of Table 1. Also, shown in FIG. 6 is an ethidium bromide stained agarose gel depicting DNA digested with EcoRI isolated from 9 independent colonies (lanes 1–9) obtained from the mAF4 BAC experiment, using EcoRI digest of the starting vector as a control (lane 10).

In the seventh experiment, a region of genomic DNA containing an ampicillin resistance gene from the yeast strain MGD 353-13D was cloned using the strategy outlined in FIG. 7. As depicted in panel A, a DNA fragment containing the p15A origin of replication, flanked by 98 or 102 bp homology arms targeted to the 98 and 102 bps flanking regions of an integrated ampicillin resistance gene in the yeast strain, MGD353-13D. The E. coli strain JC5519 was used, and expression of Redα/β was provided by the plasmid pBADαβγ-TET, followed by arabinose induction before preparation of competent cells. pBADαβγ-TET is a derivative of pBADαβγ in which the ampicillin resistance gene has been replaced by the tetracyclin resistance gene. The cloning vector was made by PCR using oligonucleotides of the following sequence:
5'-TCTTTTACTTTCACCAGCGTTTCTGGGTGAGCA AAAACAGGAAGGCAAAATGCCGCAAAAAAGG GAATAAGGGCGACACGGAAATGTTGAATACTC ATAACACCCCTTGTATTACTGTTTATGTAAGCA GACAG-3' (SEQ ID NO:13)
and
5'-TCCCGTATCGTAGTTATCTACACGACGGGGAG TCAGGCAACTATGGATGAACGAAATAGACAG ATCGCTGAGATAGGTGCCTCACTGATTAAGCA TTGGTAATTAATAAGATGATCTTCTTGAGATCG TTTTGG-3' (SEQ ID NO: 14)
to amplify the p15A origin of replication present in pACYC177. The PCR product was mixed with 4 μg NcoI digested MGD 353-13D yeast genomic DNA for cotransformation in JC5519 containing Redα/β expressed from pBADαβγ and plating on ampicillin containing plates after a 90 minute recovery period of culture in L-broth at 37° C. Clones were identified by selection for ampicillin resistance. Eighteen colonies were taken for DNA analysis. An ethidium bromide stained gel of the ten which were correct are shown in FIG. 7B.

The example described herein illustrates the success of the RecE/T and Redα/β homologous recombination cloning methods using a wide variety of circular targets—from a high copy plasmid, to a low copy large target (a BAC) to the E. coli chromosome.

The invention described and claimed herein is not to be limited in scope by the specific embodiments herein disclosed since these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. Throughout this application various references are cited, the contents of each of which is hereby incorporated by reference into the present application in its entirety for all purposes.

What is claimed is:

1. A method for introducing a double-stranded target DNA into a vector comprising culturing a bacterial cell that expresses a functional recombinase, said bacterial cell containing (a) the target DNA comprising a first double-stranded terminus and a second double-stranded terminus, and (b) a vector DNA comprising, in the following order along the vector DNA strand: (i) a first double-stranded homology arm; (ii) an origin of replication; and (iii) a second double-stranded homology arm, such that the sequence of a vector DNA strand of the first homology arm is designed to be homologous to the sequence of a target DNA strand of the first terminus, and the sequence of a vector DNA strand of the second homology arm is designed to be homologous to the sequence of the target DNA strand of the second terminus, such that the target DNA is inserted into the vector DNA between the homology arms.

2. A method for making a cell containing a recombinant DNA molecule, said method comprising:

a) introducing a first and a second strand of a double-stranded vector into a cell, said cell containing a double-stranded target DNA and expressing a bacterial recombinase, said vector comprising an origin of replication and two homology arms, in the following order from 5' to 3' along said first vector DNA strand: a first homology arm, one strand of the origin of replication, and a second homology arm;

said target DNA comprising a target DNA sequence and two termini, in the following order, from 3' to 5' along a target DNA strand: a first terminus, the target DNA sequence, and a second terminus, such that the sequence of the first homology arm on said vector DNA strand is homologous to the sequence of the first terminus on said target DNA strand, and the sequence of the second homology arm on said vector DNA strand is homologous to the sequence of the second terminus on said target DNA strand; and b) subjecting the cell to conditions that allow intracellular homologous recombination to occur.

3. A method for making a cell containing a recombinant DNA molecule, said method comprising:

a) introducing a first and a second strand of a double-stranded vector and first and second double-stranded adaptor oligonucleotides into a cell, said cell containing a double-stranded target DNA and expressing a bacterial recombinase, said vector comprising an origin of replication and two double-stranded homology arms, in the following order from 5' to 3' along said first vector DNA strand: a first homology arm, the origin of replication, and a second homology arm;

said target DNA comprising a target DNA sequence and two double-stranded termini, in the following order, from 3' to 5' along a target DNA strand: a first terminus, a target DNA sequence, and a second terminus;

said first oligonucleotide comprising a first oligonucleotide DNA strand comprising, in the following order, from 3' to 5': a first nucleotide sequence and a second nucleotide sequence, wherein said first nucleotide sequence is homologous to the nucleotide sequence of the first homology arm on said vector DNA strand, and said second nucleotide sequence is designed to be homologous to the nucleotide sequence of the first terminus on said target DNA strand;

said second oligonucleotide comprising a second oligonucleotide strand comprising, in the following order, from 3' to 5', a third nucleotide sequence and a fourth nucleotide sequence, wherein said third nucleotide sequence is homologous to the nucleotide sequence of the second homology arm on said vector DNA strand and said fourth nucleotide sequence is designed to be homologous to the nucleotide sequence of the second terminus on said target DNA strand; and b) subjecting the cell to conditions that allow intracellular homologous recombination to occur.

4. A method for making a cell containing a recombinant DNA molecule, said method comprising:

a) introducing a first and a second strand of a double-stranded target DNA molecule into a cell, said cell containing a vector and expressing a bacterial recombinase, said target DNA comprising a target DNA sequence and two double-stranded termini, in the following order, from 3' to 5' along said first target DNA strand: a first terminus, a target DNA sequence, and a second terminus;

said vector comprising an origin of replication and two homology arms, in the following order from 5' to 3' along a vector DNA strand: a first homology arm, the origin of replication and a second homology arm;

such that the sequence of the first homology arm on said vector DNA strand is designed to be homologous to the sequence of the first terminus on said first target DNA strand, and the sequence of the second homology arm on said vector DNA strand is designed to be homologous to the sequence of the second terminus on said target DNA strand; and b) subjecting the cell to conditions that allow intracellular homologous recombination to occur.

5. A method for making a cell containing a recombinant DNA molecule, said method comprising:

a) introducing a first and a second strand of a double-stranded target DNA molecule and a first and second double-stranded adaptor oligonucleotide into a cell, said cell containing a vector and expressing a bacterial recombinase, said target DNA comprising a target DNA sequence and two termini, in the following order, from 3' to 5' along said first target DNA strand: a first terminus, a target DNA sequence, and a second terminus;

said vector comprising an origin of replication and two homology arms, in the following order from 5' to 3' along a vector DNA strand: a first homology arm, the origin of replication and a second homology arm;

said first double-stranded oligonucleotide comprising a first oligonucleotide DNA strand comprising, in the following order, from 3' to 5': a first nucleotide sequence and a second nucleotide sequence, wherein said first nucleotide sequence is homologous to the nucleotide sequence of the first homology arm on said vector DNA strand, and said second nucleotide sequence is designed to be homologous to the nucleotide sequence of the first terminus on said target DNA strand;

said second double-stranded oligonucleotide comprising a second oligonucleotide strand comprising, in the following order, from 3' to 5', a third nucleotide sequence and a fourth nucleotide sequence, wherein said third nucleotide sequence is homologous to the nucleotide sequence of the second homology arm on said vector DNA strand and said fourth nucleotide sequence is designed to be homologous to the nucleotide sequence of the second terminus on said target DNA strand; and b) subjecting the cell to conditions that allow intracellular homologous recombination to occur.

6. A method for making a cell containing a recombinant DNA molecule, said method comprising:

a) introducing a first and a second strand of a double-stranded vector and a first and a second strand of a double-stranded target DNA into a cell expressing a bacterial recombinase, said double-stranded vector comprising an origin of replication and two homology arms, in the following order from 5' to 3' along said first vector DNA strand: a first homology arm, the origin of replication and a second homology arm, said double-stranded target DNA comprising a target DNA sequence and two termini, in the following order, from 3' to 5' along said first target DNA strand: a first terminus, a target DNA sequence; and a second terminus;

such that the nucleotide sequence of the first homology arm on said vector DNA strand is designed to be homologous to the nucleotide sequence of the first terminus on said target DNA strand, and the nucleotide sequence of the second homology arm on said vector DNA strand is designed to be homologous to the sequence of the second terminus on said target DNA strand; and b) subjecting the cell to conditions that allow intracellular homologous recombination to occur.

7. The method of claim 6 wherein the cell further contains a nucleotide sequence encoding a site-specific recombinase operatively linked to a promoter, and the vector further comprises a first and second recognition site for the site-specific recombinase, a first recognition site located outside the first and second homology arms, and a second site-specific recombinase recognition site located inside the first and second homology arms; and during or after step b), inducing expression of the site-specific recombinase.

8. The method of claim 6 wherein the cell further contains a nucleotide sequence encoding a site-specific endonuclease operatively linked to a promoter, and the vector further comprises a recognition site for the site-specific endonuclease located inside the first and second homology arms; and during or after step b), inducing expression of the site-specific endonuclease.

9. A method for making a cell containing a recombinant DNA molecule, said method comprising:
   a) introducing a first and a second strand of a double-stranded vector, a first and a second strand of a double-stranded target DNA molecule, and a first and second double-stranded adaptor oligonucleotide into a cell expressing a bacterial recombinase,
      said vector comprising an origin of replication and two double-stranded homology arms, in the following order from 5' to 3' along said first vector DNA strand: a first homology arm, the origin of replication and a second homology arm;
      said target DNA comprising a target DNA sequence and two double-stranded termini, in the following order, from 3' to 5' along a target DNA strand: a first terminus, the target DNA sequence, and a second terminus;
      said first oligonucleotide comprising a first oligonucleotide DNA strand comprising, in the following order, from 3' to 5': a first nucleotide sequence and a second nucleotide sequence, wherein said first nucleotide sequence is homologous to the nucleotide sequence of the first homology arm on said vector DNA strand, and said second nucleotide sequence is designed to be homologous to the sequence of the first terminus on said target DNA strand;
      said second oligonucleotide comprising a second oligonucleotide strand comprising, in the following order, from 3' to 5', a third nucleotide sequence and a fourth nucleotide sequence, wherein said third nucleotide sequence is homologous to the nucleotide sequence of the second homology arm on said vector DNA strand and said fourth nucleotide sequence is designed to be homologous to the nucleotide sequence of the second terminus on said target DNA strand; and
   b) subjecting the cell to conditions that allow intracellular homologous recombination to occur.

10. The method of claim 9 wherein the cell further contains a nucleotide sequence encoding a site-specific recombinase operatively linked to a promoter, and the vector further comprises a first and second recognition site for the site-specific recombinase, a first recognition site located outside the first and second homology arms, and a second site-specific recombinase recognition site located inside the first and second homology arms; and during or after step b), inducing expression of the site-specific recombinase.

11. The method of claim 9 wherein the cell further contains a nucleotide sequence encoding a site-specific endonuclease operatively linked to a promoter, and the vector further comprises a recognition site for the site-specific endonuclease located inside the first and second homology arms; and during or after step b), inducing expression of the site-specific endonuclease.

12. The method of any one of claims 2–11 wherein the vector further comprises a selectable marker located outside the first and second homology arms, such that the vector comprises, in either of the following two orders from 5' to 3' along a vector DNA strand: i) the first homology arm, the selectable marker, the origin of replication and the second homology arm, or ii) the first homology arm, the origin of replication, the selectable marker, and the second homology arm.

13. The method of any one of claims 2–11 wherein the bacterial recombinase is RecE/T or Redα/β recombinase or both RecE/T and Redα/β recombinases.

14. The method of any one of claims 2–11 wherein the cell is a bacterial cell.

15. The method of any one of claims 2–11 wherein the cell is an E. coli cell.

16. The method of any one of claims 2–11 wherein the cell is a eukaryotic cell that recombinantly expresses RecE/T and/or Redα/β recombinase.

17. A method for making a recombinant DNA molecule comprising the method of any one of claims 2–11 which further comprises isolating a recombinant DNA molecule that comprises the target DNA sequence inserted into the vector.

18. The method of any one of claims 2–11 wherein the target DNA is known or suspected to be associated with a disorder or disease when genetically mutated.

19. The method of any one of claims 2–11 wherein the target DNA is a bacterial, viral, parasite, or protozoan DNA.

20. The method of claims 2, 4, 6, 7, or 8 which further comprises detecting a recombinant DNA molecule that comprises the target DNA inserted into the vector.

21. A method of detecting the presence of an infectious agent comprising carrying out the method of claim 20, wherein the target DNA is derived from a patient suspected of having an infectious disease, and the sequences of the first and second homology arms are homologous to the sequences present in DNA of the infectious agent.

22. The method of any one of claims 2–9 wherein the cell is an embryonic stem cell.

23. The method of claim 12 wherein the selectable marker confers antibiotic resistance to the cell containing the vector.

24. A cell comprising a double-stranded DNA vector useful for directed cloning or subcloning of a target DNA molecule of interest, said vector comprising an origin of replication and two homology arms, in the following order from 5' to 3' along a vector DNA strand: a first homology arm, the origin of replication and a second homology arm; such that the nucleotide sequence of the first homology arm on a first vector DNA strand is designed to be homologous to the sequence of a first terminus on a first target DNA strand, and the nucleotide sequence of the second homology arm on the first vector DNA strand is designed to be homologous to the nucleotide sequence of a second terminus on the first target DNA strand.

25. The cell of claim 24 which is a bacterial cell.

26. A kit useful for directed cloning or subcloning of a target DNA molecule comprising in one or more containers:
   a) a double-stranded DNA vector useful for directed cloning or subcloning of a target DNA molecule of interest, said vector comprising an origin of replication and two homology arms, in the following order from 5' to 3' along a vector DNA strand: a first homology arm, the origin of replication and a second homology arm; such that the nucleotide sequence of the first homology arm on a first vector DNA strand is designed to be homologous to the sequence of a first terminus on a first target DNA strand, and the nucleotide sequence of the second homology arm on the first vector DNA strand is designed to be homologous to the nucleotide sequence of a second terminus on the first target DNA strand; and b) a cell containing a bacterial recombinase.

27. The kit of claim 26 wherein the homology arms have sequence homology to a BAC, PAC, lambda, plasmid or YAC based cloning vector.

28. A kit useful for directed cloning or subcloning of a target DNA molecule comprising in one or more containers:

c) a double-stranded DNA vector useful for directed cloning and subcloning of a target DNA molecule of interest, said vector comprising an origin of replication and two homology arms, in the following order from 5' to 3' along a vector DNA strand: a first homology arm, the origin of replication and a second homology arm; and d) a first double-stranded adaptor oligonucleotide comprising a first oligonucleotide DNA strand comprising, in the following order, from 3' to 5': a first sequence and a second sequence, wherein said first nucleotide sequence is homologous to the nucleotide sequence of the first homology arm on said vector DNA strand, and said second nucleotide sequence is designed to be homologous to the nucleotide sequence of a first terminus on a target DNA strand;

e) a second double-stranded adaptor oligonucleotide comprising a second oligonucleotide strand comprising, in the following order, from 3' to 5': a third nucleotide sequence and a fourth nucleotide sequence, wherein said third nucleotide sequence is homologous to the nucleotide sequence of the second homology arm on said vector DNA strand and said fourth nucleotide sequence is designed to be homologous to the nucleotide sequence of a second terminus on said target DNA strand; and f) a cell containing a bacterial recombinase.

29. The kit of claim 26 or 28 wherein the cell is an *E. coli* cell.

30. The kit of claim 26 or 28 wherein the cell is a frozen cell competent for uptake of DNA.

31. A kit useful for directed cloning or subcloning of a target DNA molecule comprising in one or more containers:

a) a double-stranded DNA vector useful for directed cloning and subcloning of a target DNA molecule of interest, said vector comprising an origin of replication and two homology arms, in the following order from 5' to 3' along a vector DNA strand: a first homology arm, the origin of replication and a second homology arm;

b) a first double-stranded adaptor oligonucleotide comprising a first oligonucleotide DNA strand comprising, in the following order, from 3' to 5': a first nucleotide sequence and a second nucleotide sequence, wherein said first nucleotide sequence is homologous to the nucleotide sequence of the first homology arm on said vector DNA strand, and said second nucleotide sequence is designed to be homologous to the nucleotide sequence of a first terminus on a target DNA strand; and c) a second double-stranded adaptor oligonucleotide comprising a second oligonucleotide strand comprising, in the following order, from 3' to 5': a third nucleotide sequence and a fourth nucleotide sequence, wherein said third nucleotide sequence is homologous to the nucleotide sequence of the second homology arm on said vector DNA strand and said fourth sequence is designed to be homologous to the nucleotide sequence of a second terminus on said target DNA strand.

32. The kit of claim 26, 28, or 31 wherein the DNA vector is purified.

33. The kit of claim 28 or 31 wherein the DNA vector, the first double-stranded oligonucleotide, and the second double-stranded oligonucleotide are purified.

34. The kit of claims 26, 28, or 31 wherein the target DNA molecule comprises bacterial, viral, parasite, or protozoan DNA.

35. The kit of claims 26, 28, or 31 wherein the target DNA molecule comprises a genetic mutation or polymorphism known or suspected to be associated with a disorder or disease.

36. The kit of any one of claims 25, 26, or 28 wherein the bacterial recombinase is RecE/T or Redα/β recombinase or both RecE/T and Redα/β recombinases.

37. The kit of claim 28 or 31 wherein the first and second double-stranded oligonucleotide have nucleotide sequence homology to a BAC, PAC, lambda, plasmnid or YAC based cloning vector.

38. A method of detecting the presence of an infectious agent comprising carrying out the method of claim 21, wherein the target DNA is derived from a patient suspected of having an infectious disease, and said second and fourth nucleotide sequences are homologous to sequences present in DNA of the infectious agent.

39. A method of detecting the presence of a genetic condition, genetic disease, genetic disorder, or polymorphic trait comprising carrying out the method of claim 20, wherein the target DNA is derived from a patient suspected of having a genetic condition, disease, disorder, or polymorphic trait, and the sequence of the first homology arm is homologous to a sequence upstream from a site known or suspected to be associated with the genetic condition, disease, disorder, or polymorphic trait, and the sequence of the second homology arm is homologous to a sequence downstream from a site known or suspected to be associated with the genetic condition, disease, disorder, or polymorphic trait.

40. The method of claim 38 wherein the infectious agent is a virus, bacteria, protozoa, fungus, or parasite.

41. A method of detecting the presence of a genetic condition, genetic disease, genetic disorder, or polymorphic trait comprising carrying out the method of claim 21, wherein the target DNA is derived from a patient suspected of having the genetic condition, genetic disease, genetic disorder, or polymorphic trait, and the sequence of the first double-stranded oligonucleotide is homologous to a sequence upstream from a site known or suspected to be associated with the genetic condition, genetic disease, genetic disorder, or polymorphic trait, and the sequence of the second double-stranded oligonucleotide is homologous to a sequence downstream from a site known or suspected to be associated with the genetic condition, genetic disease, genetic disorder, or polymorphic trait.

42. The method of claim 38 or 40 wherein the infectious agent is a virus, bacteria, protozoa, fungus, or parasite.

43. The method of claim 39 wherein the genetic condition, genetic disease, genetic disorder, or polymorphic trait is or predisposes the patient to cancer, asthma, arthritis, drug resistance, drug toxicity, or a neural, neuropsychiatric, metabolic, muscular, cardiovascular, or skin condition, disease or disorder.

44. The method of claim 40 wherein the infectious agent is a virus, bacteria, protozoa, fungus, or parasite.

45. The method of claim 41 wherein the genetic condition, genetic disease, genetic disorder, or polymorphic trait is or predisposes the patient to cancer, asthma, arthritis, drug resistance, drug toxicity, or a neural, neuropsychiatric, metabolic, muscular, cardiovascular, or skin condition, disease or disorder.

46. A method for making a double-stranded DNA vector useful for directed cloning or subcloning of a target DNA molecule of interest, comprising incorporating first and second homology arms into a double-stranded DNA molecule, wherein the double-stranded DNA molecule comprises an origin of replication, in the following order from 5' to 3' along a vector DNA strand: a first homology arm, the origin of replication, and a second homology arm, such that the nucleotide sequence of the first homology arm on a first vector DNA strand is designed to be homologous to the sequence of the first terminus on a first target DNA strand, and the nucleotide sequence of the second homology arm on the first vector DNA strand is designed to be homologous to the nucleotide sequence of the second terminus on the first target DNA strand, wherein said target DNA molecule comprises a target DNA sequence and two termini, in the following order, from 3' to 5' along a target DNA strand: a first terminus, the target DNA sequence, and a second terminus.

47. A method for making a double-stranded DNA vector useful for directed cloning or subcloning of a target DNA molecule of interest, comprising:
   a) choosing two homology arms, such that the sequence of the first homology arm is designed to be homologous to the sequence of a first terminus on a target DNA strand, and the sequence of the second homology arm is designed to be homologous to the sequence of a second terminus on the target DNA strand, wherein the target DNA comprises a target DNA sequence and two double-stranded termini, in the following order, from 3' to 5' along a target DNA strand: the first terminus, the target DNA sequence, and the second terminus; and
   b) constructing a vector by incorporating the two homology arms into a DNA molecule comprising an origin of replication in the following order from 5' to 3' along a vector DNA strand: the first homology arm, the origin of replication and the second homology arm.

48. The method of claim 46 or 47 wherein the origin of replication is a bacterial origin of replication.

49. The method of claim 46 or 47 wherein the origin of replication functions in *E. coli*.

50. The method of claim 46 or 47 wherein the origin of replication functions in a mammalian cell.

51. A method for making a recombinant DNA molecule comprising making a double-stranded vector according to the method of claim 46 or 47, further comprising the steps of.
   b) introducing the target DNA molecule into a cell, said cell containing the vector and expressing a bacterial recombinase; and
   c) subjecting the cell to conditions that allow intracellular homologous recombination to occur.

52. A method for making a recombinant DNA molecule comprising making a double-stranded vector according to the method of claim 46 or 47, further comprising the steps of:
   b) introducing the target DNA molecule and the vector into a cell, said cell expressing a bacterial recombinase; and
   c) subjecting the cell to conditions that allow intracellular homologous recombination to occur.

53. A method for making a recombinant DNA molecule comprising:
   a) preparing first and second double-stranded adaptor oligonucleotides, wherein said first oligonucleotide comprises a first oligonucleotide DNA strand comprising, from 3' to 5', a first nucleotide sequence and a second nucleotide sequence, wherein said first nucleotide sequence is homologous to the nucleotide sequence of a first homology arm on a vector DNA strand and said second nucleotide sequence is designed to be homologous to the nucleotide sequence of a first terminus on a target DNA strand, and wherein said second oligonucleotide comprises a second oligonucleotide strand comprising, from 3' to 5', a third nucleotide sequence and a fourth nucleotide sequence, wherein said third nucleotide sequence is homologous to the nucleotide sequence of a second homology arm on said vector DNA strand and said fourth nucleotide sequence is designed to be homologous to the nucleotide sequence of a second terminus on said target DNA strand;
   wherein said vector comprises an origin of replication and two homology arms, in the following order from 5' to 3' along a vector DNA strand: a first homology arm, an origin of replication and a second homology arm, wherein said target DNA comprises a target DNA sequence and two termini, in the following order, from 3' to 5' along a target DNA strand: a first terminus, a target DNA sequence;
   b) introducing the target DNA and the first and second double-stranded oligonucleotide into a cell, said cell containing a vector and expressing a bacterial recombinase; and
   c) subjecting the cell to conditions that allow intracellular homologous recombination to occur.

54. A method for making a recombinant DNA molecule comprising:
   a) preparing first and second double-stranded adaptor oligonucleotides, wherein said first oligonucleotide comprises a first oligonucleotide DNA strand comprising, from 3' to 5', a first nucleotide sequence and a second nucleotide sequence, wherein said first nucleotide sequence is homologous to the nucleotide sequence of a first homology arm on a vector DNA strand and said second nucleotide sequence is designed to be homologous to the nucleotide sequence of a first terminus on a target DNA strand, and wherein said second oligonucleotide comprises a second oligonucleotide strand comprising, from 3' to 5', a third nucleotide sequence and a fourth nucleotide sequence, wherein said third nucleotide sequence is homologous to the nucleotide sequence of a second homology arm on said vector DNA strand and said fourth nucleotide sequence is designed to be homologous to the nucleotide sequence of a second terminus on said target DNA strand;
   b) introducing the vector, the target DNA, and the first and second double-stranded oligonucleotide into a cell expressing a bacterial recombinase; and
   c) subjecting the cell to conditions that allow intracellular homologous recombination to occur.

* * * * *

SEQUENCE LISTING

<160> NUMBER OF SEQ ID NOS: 14

<210> SEQ ID NO 1
<211> LENGTH: 84
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 1
ttcctctgta ttaaccgggg aatacagtgt aatcgataat tcagaggaat agctcgagtt    60
aataagatga tcttcttgag atcg                                          84

<210> SEQ ID NO 2
<211> LENGTH: 83
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 2
cagcaatgtc atcgagctga gacttactga taccgggacc cgcgtggtaa ttctcgagtg    60
attagaaaaa ctcatcgagc atc                                           83

<210> SEQ ID NO 3
<211> LENGTH: 92
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 3
tcaacattaa atgtgagcga gtaacaaccc gtcggattct ccgtgggaac aaacgggaat    60
tctgattaga aaaactcatc gagcatcaaa tg                                 92

<210> SEQ ID NO 4
<211> LENGTH: 83
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 4 tcagggaaa accttattta tcagccggaa aacctaccgg attgatggta gggatcctta     60
ataagatgat cttcttgaga tcg                                           83

<210> SEQ ID NO 5
<211> LENGTH: 92
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 5
tcaacattaa atgtgagcga gtaacaaccc gtcggattct ccgtgggaac aaacgggaat    60
tctgattaga aaaactcatc gagcatcaaa tg                                 92

<210> SEQ ID NO 6
<211> LENGTH: 83
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 6 tcagggaaa accttattta tcagccggaa aacctaccgg attgatggta gggatcctta    60
ataagatgat cttcttgaga tcg                                          83

<210> SEQ ID NO 7
<211> LENGTH: 89
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 7
tgcactttga tatcgaccca agtaccgcca cctaacaatt cgttcaagcc gaggatcctt    60
aataagatca tcttctgaga tcgttttgg                                     89

<210> SEQ ID NO 8
<211> LENGTH: 90
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 8
tgcattacag tttacgaacc gaacaggctt atgtcaactg ggttcgtgcc ttcagaattc    60
tgattagaaa aactcatcga gcatcaaatg                                    90

<210> SEQ ID NO 9
<211> LENGTH: 92
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 9
tcaacattaa atgtgagcga gtaacaaccc gtcggattct ccgtgggaac aaacgggaat    60
tctgattaga aaaactcatc gagcatcaaa tg                                 92

<210> SEQ ID NO 10
<211> LENGTH: 83
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 10 tcagggaaa accttattta tcagccggaa aacctaccgg attgatggta gggatcctta    60
ataagatgat cttcttgaga tcg                                          83

<210> SEQ ID NO 11
<211> LENGTH: 101
<212> TYPE: DNA

```
<213> ORGANISM: Artificial Sequence
<220> FEATURE:
<223> OTHER INFORMATION: Description of Artificial Sequence:
      Oligonucleotide

<400> SEQUENCE: 11
tgtagctgag cccaggggca aggctgcttt gtaccagcct gctgtctgcg ggggcatcac     60
ctggaattct taataagatg atcttcttga gatcgttttg g                       101

<210> SEQ ID NO 12
<211> LENGTH: 98
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 12
tgggtgtcaa cctcaggctt tctcacacgc aatacaggta gggacttgca cccctacaca    60
ccgaattctg attagaaaaa ctcatcgagc atcaaatg                            98

<210> SEQ ID NO 13
<211> LENGTH: 134
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 13
tcttttactt tcaccagcgt ttctgggtga gcaaaaacag gaaggcaaaa tgccgcaaaa    60
aagggaataa gggcgacacg gaaatgttga atactcataa caccccttgt attactgttt   120
atgtaagcag acag                                                     134

<210> SEQ ID NO 14
<211> LENGTH: 134
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 14
tcccgtatcg tagttatcta cacgacgggg agtcaggcaa ctatggatga acgaaataga    60
cagatcgctg agataggtgc ctcactgatt aagcattggt aattaataag atgatcttct   120
tgagatcgtt ttgg                                                     134
```